(12) United States Patent
Dudley et al.

(10) Patent No.: US 10,543,219 B2
(45) Date of Patent: *Jan. 28, 2020

(54) ORAL TESTOSTERONE ESTER FORMULATIONS AND METHODS OF TREATING TESTOSTERONE DEFICIENCY COMPRISING SAME

(71) Applicant: Clarus Therapeutics, Inc., Northbrook, IL (US)

(72) Inventors: Robert E. Dudley, Murfreesboro, TN (US); Panayiotis P. Constantinides, Gurnee, IL (US)

(73) Assignee: Clarus Therapeutics, Inc., Northbrook, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/723,985

(22) Filed: Oct. 3, 2017

(65) Prior Publication Data

US 2018/0110786 A1    Apr. 26, 2018

Related U.S. Application Data

(63) Continuation of application No. 15/381,430, filed on Dec. 16, 2016, which is a continuation of application No. 14/290,540, filed on May 29, 2014, now abandoned, which is a continuation of application No. 13/584,958, filed on Aug. 14, 2012, now Pat. No. 8,778,916, which is a continuation of application No. 12/758,770, filed on Apr. 12, 2010, now Pat. No. 8,492,369.

(51) Int. Cl.
| | |
|---|---|
| A61K 31/568 | (2006.01) |
| A61K 9/107 | (2006.01) |
| A61K 9/00 | (2006.01) |
| A61K 47/12 | (2006.01) |
| A61K 47/44 | (2017.01) |

(52) U.S. Cl.
CPC .......... *A61K 31/568* (2013.01); *A61K 9/0053* (2013.01); *A61K 9/0095* (2013.01); *A61K 9/107* (2013.01); *A61K 47/12* (2013.01); *A61K 47/44* (2013.01)

(58) Field of Classification Search
CPC ...... A61K 31/568; A61K 47/12; A61K 47/44; A61K 9/107; A61K 9/0053
See application file for complete search history.

(56) References Cited

U.S. PATENT DOCUMENTS

| | | |
|---|---|---|
| 3,164,520 A | 1/1965 | Charles |
| 3,266,991 A | 8/1966 | Albert |
| 4,147,783 A | 4/1979 | Van Der Vies |
| 4,220,599 A | 9/1980 | van der Vies |
| 4,572,915 A | 2/1986 | Crooks |
| 4,719,239 A | 1/1988 | Muller |
| 5,342,625 A | 8/1994 | Hauer |
| 5,605,929 A | 2/1997 | Liao |
| 5,645,856 A | 7/1997 | Lacy |
| 5,891,469 A | 4/1999 | Amselem |
| 6,013,665 A | 1/2000 | DeMichele |
| 6,054,136 A | 4/2000 | Farah |
| 6,096,338 A | 8/2000 | Lacy |
| 6,140,375 A | 10/2000 | Nagahama |
| 6,160,007 A | 12/2000 | DeMichele |
| 6,191,105 B1 | 2/2001 | Ekwuribe |
| 6,248,363 B1 | 6/2001 | Patel |
| 6,267,985 B1 | 7/2001 | Chen |
| 6,280,770 B1 | 8/2001 | Pather |
| 6,294,192 B1 | 9/2001 | Patel |
| 6,303,662 B1 | 10/2001 | Nagahama |
| 6,306,434 B1 | 10/2001 | Hong |
| 6,309,663 B1 | 10/2001 | Patel |
| 6,309,665 B2 | 10/2001 | Barthelemy |
| 6,312,704 B1 | 11/2001 | Farah |
| 6,383,471 B1 | 5/2002 | Chen |
| 6,451,339 B2 | 9/2002 | Patel |
| 6,458,383 B2 | 10/2002 | Chen |
| 6,569,463 B2 | 5/2003 | Patel |
| 6,623,765 B1 | 9/2003 | Dennis |
| 6,652,880 B1 | 11/2003 | Aylwin |
| 6,665,880 B2 | 12/2003 | Poppe |
| 6,761,903 B2 | 7/2004 | Chen |
| 6,923,988 B2 | 8/2005 | Patel |
| 6,982,281 B1 | 1/2006 | Chen |
| 7,025,979 B2 | 4/2006 | Nieschlag |
| 7,374,779 B2 | 5/2008 | Chen |
| 8,367,103 B2 | 2/2013 | Bardani |
| 8,492,369 B2 | 7/2013 | Dudley |
| 8,778,916 B2 | 7/2014 | Dudley |

(Continued)

FOREIGN PATENT DOCUMENTS

| | | |
|---|---|---|
| CN | 1686143 | 10/2005 |
| EP | 0904064 B1 | 10/2001 |

(Continued)

OTHER PUBLICATIONS

A.T. Burbello at al., Sovremennye Iekarstvennyesredstva S-Pb 'Neva', 2004, p. 567. (partial translation only).
Addo et al., 'Non-polar extracts of serum from males contain covert radioimmunoassayable testosterone,' [on line] (abstract, database PubMed PMID: 2588302) (found Nov. 19, 2009), Sep. 1989, pp. 257-269, vol. 54, No. 3.
Andriol Testocaps Consumer Medicine Information, Sep. 2003.
Cantrill, J. et al., Which Testosterone Replacement Therapy?, 1984, Clinical Endocrinology vol. 21, pp. 97-107.

(Continued)

*Primary Examiner* — Matthew P Coughlin
*Assistant Examiner* — Thurman Wheeler
(74) *Attorney, Agent, or Firm* — Dennis A. Bennett; Brock D. Levin

(57) ABSTRACT

A pharmaceutical formulation of testosterone undecanoate is provided. Methods of treating a testosterone deficiency or its symptoms with the inventive formulations are also provided.

12 Claims, 5 Drawing Sheets

(56) References Cited

U.S. PATENT DOCUMENTS

| | | |
|---|---|---|
| 8,778,922 B2 | 7/2014 | Giliyar |
| 8,865,695 B2 | 10/2014 | Giliyar |
| 9,034,858 B2 | 5/2015 | Giliyar |
| 9,205,057 B2 | 12/2015 | Giliyar |
| 9,358,241 B2 | 6/2016 | Giliyar |
| 9,480,690 B2 | 11/2016 | Giliyar |
| 9,757,390 B2 | 9/2017 | Giliyar |
| 2001/0018069 A1 | 8/2001 | Johnson |
| 2002/0068693 A1 | 6/2002 | Jeng |
| 2003/0022875 A1 | 1/2003 | Wilson |
| 2003/0072798 A1 | 4/2003 | Schwarz |
| 2003/0104048 A1 | 6/2003 | Patel |
| 2003/0180352 A1 | 9/2003 | Patel |
| 2003/0186892 A1 | 10/2003 | Taneja |
| 2003/0235595 A1 | 12/2003 | Chen |
| 2003/0236236 A1 | 12/2003 | Chen |
| 2004/0002445 A1 | 1/2004 | Taneja |
| 2004/0115287 A1 | 6/2004 | Chen |
| 2004/0127476 A1 | 7/2004 | Kershman |
| 2005/0096296 A1 | 5/2005 | Fikstad |
| 2005/0096365 A1 | 5/2005 | Fikstad |
| 2005/0100608 A1 | 5/2005 | Ebert |
| 2005/0101517 A1 | 5/2005 | De Nijs |
| 2005/0129718 A1 | 6/2005 | Sherman |
| 2005/0171193 A1 | 8/2005 | Chen |
| 2005/0176692 A1 | 8/2005 | Amory |
| 2005/0287203 A1 | 12/2005 | Nijs |
| 2006/0003002 A1 | 1/2006 | Fikstad |
| 2006/0034937 A1 | 2/2006 | Patel |
| 2007/0232548 A1 | 10/2007 | Taneja |
| 2008/0020053 A1 | 1/2008 | Persson |
| 2008/0217692 A1 | 9/2008 | Anderson |
| 2008/0317844 A1 | 12/2008 | Dudley |
| 2008/0317850 A1 | 12/2008 | Hewitt |
| 2009/0074859 A1 | 3/2009 | Patel |
| 2010/0136105 A1 | 6/2010 | Chen |
| 2010/0137271 A1 | 6/2010 | Chen |
| 2010/0173882 A1 | 7/2010 | Giliyar |
| 2011/0039814 A1 | 2/2011 | Huatan |
| 2011/0142945 A1 | 6/2011 | Chen |
| 2011/0251167 A1 | 10/2011 | Dudley |
| 2012/0135069 A1 | 5/2012 | Keck |
| 2012/0135074 A1 | 5/2012 | Giliyar |
| 2012/0148675 A1 | 6/2012 | Chickmath |
| 2012/0244215 A1 | 9/2012 | Giliyar |
| 2012/0309731 A1 | 12/2012 | Dudley |
| 2012/0322780 A1 | 12/2012 | Giliyar |
| 2013/0045271 A1 | 2/2013 | Dadey |
| 2013/0052263 A1 | 2/2013 | Fikstad |
| 2013/0225544 A1 | 8/2013 | Nachaegari |
| 2013/0303495 A1 | 11/2013 | Dhingra |
| 2014/0178466 A1 | 6/2014 | Giliyar |
| 2014/0274986 A1 | 9/2014 | Dudley |
| 2014/0303129 A1 | 10/2014 | Dudley |
| 2014/0309202 A1 | 10/2014 | Giliyar |
| 2015/0038475 A1 | 2/2015 | Chickmath |
| 2015/0190406 A1 | 7/2015 | Giliyar |
| 2015/0320765 A1 | 11/2015 | Giliyar |
| 2016/0367569 A1 | 12/2016 | Giliyar |
| 2017/0007622 A1 | 1/2017 | Giliyar |
| 2017/0106002 A1 | 4/2017 | Dudley |
| 2017/0216312 A1 | 8/2017 | Giliyar |
| 2017/0246184 A1 | 8/2017 | Dudley |
| 2017/0246186 A1 | 8/2017 | Giliyar |
| 2017/0252357 A1 | 9/2017 | Giliyar |

FOREIGN PATENT DOCUMENTS

| | | |
|---|---|---|
| EP | 1189620 | 7/2012 |
| EP | 2558073 | 2/2013 |
| GB | 1264677 | 2/1972 |
| GB | 2228198 A | 8/1990 |
| WO | 1992018147 A1 | 10/1992 |
| WO | 1993002664 A1 | 2/1993 |
| WO | 199408610 A1 | 4/1994 |
| WO | 9524893 | 9/1995 |
| WO | 199524893 A1 | 9/1995 |
| WO | 1995024893 | 9/1995 |
| WO | 199740823 A1 | 11/1997 |
| WO | 199834621 | 8/1998 |
| WO | 0059482 | 10/2000 |
| WO | 20059512 A1 | 10/2000 |
| WO | 200059482 A1 | 10/2000 |
| WO | 200101960 | 11/2001 |
| WO | 20010187316 | 11/2001 |
| WO | 2002015938 | 2/2002 |
| WO | 2003026649 | 4/2003 |
| WO | 2005081742 A2 | 9/2005 |
| WO | 2006013369 A2 | 2/2006 |
| WO | 2006113505 A2 | 10/2006 |
| WO | 2006119498 A2 | 11/2006 |
| WO | 2007018943 A2 | 2/2007 |
| WO | 2010081032 A2 | 7/2010 |
| WO | 2011082384 A2 | 7/2011 |
| WO | 2011129812 | 10/2011 |
| WO | 2011129812 A1 | 10/2011 |
| WO | 2012075081 A2 | 6/2012 |
| WO | 2012079092 A2 | 6/2012 |
| WO | 2012092202 A2 | 7/2012 |
| WO | 2014145518 | 9/2014 |

OTHER PUBLICATIONS

Chandrashekar G. et al., U.S. Appl. No. 13/485,807 not yet published. Continuation of US application publication No. US/2012/0135074 published May 31, 2012.

Constantinides, P., 'Lipid Microemulsions for Improving Drug Dissolution and Oral Absorption: Physical and Biopharmaceutical Aspects,' Pharmaceutical Research, 1995, pp. 1561-1572, vol. 12, No. 11.

EPO Application 10714521.1—Decision to Grant dated Mar. 20, 2014—Dudley, Robert, E. et al., Oral Testosterone Ester Formulations and Methods of Treating Testosterone Deficiency Comprising Same.

Graham-Smith et al., 'The Oxford Reference-book on Clinical Pharmacology and Pharmacotherapy', M. Meditsina Publishers, 2000, pp. 25, 136-137 (partial translation).

International Search Report and Written Opinion dated Dec. 1, 2010, in International Application No. PCT/US2010/030788.

MacGregor, KJ, et al., 'Influence of lipolysis on drug absorption from the gastro-intestinal tract,' Advanced Drug Delivery Reviews 25 (1997) 33-46.

Maisey et al., 'Clinical Efficacy of Testosterone Undecanoate in Male Hypogonadism,' Clinical Endocrinology, 1981, pp. 625-629, vol. 14.

Noguchi, T, et al., 'The effect of drug lipophilicity and lipid vehicles on the lymphatic absorption of various testosterone,' International Journal of Pharmaceutics, 24 (1985) 173-184.

Patent Interference No. 106,045; Decision on Motions; Sep. 20, 2017; 33 pages.

S. Yu. Kalinchenko 'Testosteron-korol' gormonov I gormon korolei'. The Journal 'Sex and Life', 2004, pp. 12-22 / online [retrieved on Mar. 26, 2010 13:27]. Retrieved from the Internet: URL:http://www.lazmed.ru/interesting/publications/testosteron.html. (partial translation only).

Shackleford et al.: "Contribution of Lymphatically Transported Testosterone Undecanoate to the Systemic Exposure of Testosterone after Oral Administration of Two Andriol Formulations in Conscious Lymph Duct-Cannulated Dogs", The Journal of Pharmacology and Experimental Therapeutics, vol. 306, No. 3, pp. 925-933.

Tenover J Lisa, 'The androgen-deficient aging male: current treatment options.', Reviews in Urology 2003 LNKD-PUBMED:16985939, (2003), vol. 5 Suppl 1, ISSN 1523-6161, pp. S22-S28, XP002665568.

Tso, et al., 'Intestinal Absorption and Lymphatic Transport of a High Linolenic Acid Canola Oil in Lymph Fistula Sprague-Dawley Rats', American Society for Nutritional Sciences, 2002, pp. 218-221.

Wacher, V.J. et al. Peppermint Oil Enhances Cyclosporine Oral Bioavailability in Rats: Comparison With D-a-Tocopheryl Poly(ethylene glycol 1000) Succinate (TPGS) and Ketoconazole; J. Pharm. Sci. vol. 91, No. 1. p. 77-90, 2002.

(56) References Cited

OTHER PUBLICATIONS

Yin, A. et al., Dietary Fat Modulates the Testosterone Pharmacokinetics of a New Self-Emulsifying Formulation of Oral Testosterone Undecanoate in Hypogonadal Men, 2012, Journal of Andrology.
Yin, A. et al., Reexamination of Pharmacokinetics of Oral Testosterone Undecanoate in Hypogonadal Men With a New Self-Emulsifying Formulation, 2012, Journal of Andrology, vol. 33, No. 2, pp. 190-201.
Al-Sukhun, et al., "Lipid Drug Delivery Systems and Their Fate after Oral Administration," Ph.D. Dissertation, University of Bath, UMI No. U601432, ProQuest LLC: Ann Arbor, MI (2002).
Amory, et al., "Oral testosterone in Oil Plus Dutasteride in Men: A Pharmacokinetic Study," J. Clin Endocrinol. & Metab., 90(5): 2610-2617 (2005).
Anby, et al., "Lipid Digestion as a Trigger for Supersaturation: Evaluation of the Impact of Supersaturation Stabilization on the in Vitro and in Vivo Performance of Self-Emulsifying Drug Delivery Systems," Mol. Pharm., 9: 2063-2079 (2012).
Ansari, et al., "Microemulsions as Potential Drug Delivery Systems: A Review," PDA J Pharm. Sci. Tech., 62(1): 66-79 (2008).
Araya, et al., "The novel formulation design of O/W microemulsion for improving the gastrointestinal absorption of poorly water soluble compounds, " Int. J. Pharm., 305: 61-74 (2005).
Araya, et al., "The Novel Formulation Design of Self-emulsifying Drug Delivery Systems (SEDDS) Type O/W Microemulsion I: Enhancing Effects on Oral Bioavailability of Poorly Water Soluble Compounds in Rats and Beagle Dogs," Drug Metab. Pharmacokinet., 20(4): 244-256 (2005).
Bittner, et al., "Formulations and Related Activities for the Oral Administration of Poorly Water-soluble Compounds in Early Discovery Animal Studies," Drugs made in Germany, 45(1): 18-24 (2002).
Bittner, et al., "Formulations and Related Activities for the Oral Administration of Poorly Water-soluble Compounds in Early Discovery Animal Studies," Pharm. Ind., 64(8): 800-807 (2002).
Bowtle, et al., "Materials, Process, and Manufacturing Considerations for Lipid-Based Hard-Capsule Formats," Chapter 4, pp. 79-106, in Oral Lipid Based Formulations; Enhancing the Bioavailability of Poorly Water-Soluble Drugs, Hauss, ed., Informa Healthcare USA, Inc.: New York, NY (2007).
Brouwers, et al., "Supersaturating drug delivery systems: The answer to solubility-limited oral bioavailability?," J. Pharm. Sci., 98(8): 2549-2572 (2009).
Chakraborty, et al., "Lipid: an emerging platform for oral delivery of drugs with poor bioavailability," Eur. J. Pharm. Biopharm., 73: 1-15 (2009).
Chambin, et al., "Interest of multifunctional lipid excipients: Case of Gelucire1 44/14," Drug Dev. Ind. Pharm., 31: 527-534 (2005).
Charman, "Lipids, lipophilic drugs, and oral drug delivery-some emerging concepts," J. Pharm. Sci., 89: 967-978 (2000).
Charman, et al., "Absorption of danazol after administration to different sites of the gastrointestinal tract and the relationship to single- and doublepeak phenomena in the plasma profiles," J. Clin.Pharmacol., 33: 1207-1213 (1993).
Charman, et al., "Effect of food and a monoglyceride emulsion formulation on danazol bioavailability," J. Clin. Pharmacol., 33: 381-386 (1993).
Charman, et al., "Effects of lipid class and lipid vehicle volume on the intestinal lymphatic transport of DDT," Int. J. Pharm. 33: 165-172 (1986).
Charman, Susan A. et al., "Self-Emulsifying Drug Delivery Systems: Formulation and Biopharmaceutic Evaluation of an Investigational Lipophilic Compound", Pharmaceutical Research 9(1):87-93, (1992).
Cheema, et al., "Lipid vehicles for intestinal lymphatic drug absorption," J. Pharm. Pharmacol., 39: 55-56 (1987).
Christensen, et al., "Solubilisation of poorly water-soluble drugs during in vitro lipolysis of medium- and long-chain triacylglycerols," Eur. J. Pharm. Sci., 23: 287-296 (2004).
Constantinides, et al., "Formulation and Intestinal Absorption Enhancement Evaluation of Water-in-Oil Microemulsions Incorporating Medium-Chain Glycerides," Pharm. Res., 11(10): 1385-1390 (1994).
Constantinides, et al., "Advances in lipid-based drug solubilization and targeting," Adv. Drug Del. Rev., Preface, 56(9): 1239-1240 (2004).
Constantinides, et al., "Tocol emulsions for drug solubilization and parenteral delivery," Adv. Drug Del. Rev., 56: 1243-1255 (2004).
Constantinides, et al., "Advances in lipid nanodispersions for parenteral drug delivery and targeting," Adv. Drug Del. Rev., 60: 757-767 (2008).
Constantinides, et al., "Advances in the Use of Tocols as Drug Delivery Vehicles," Pharm. Res., 23(2): 243-255 (2006).
Constantinides, et al., "Formulation and physical characterization of water-in-oil microemulsions containing long versus medium-chain glycerides," Int. J. Pharm., 158: 57-68 (1997).
Constantinides, et al., "Formulation Development and Antitumor Activity of a Filter-Sterilizable Emulsion of Paclitaxel," Pharm. Res., 17(2): 175-182 (2000).
Constantinides, et al., "Lipid Formulation Strategies for Enhancing Intestinal Transport and Absorption of P-Glycoprotein (P-gp) Substrate Drugs: in vitro/in vivo Case Studies," J. Pharm. Sci., 96: 235-248 (2007).
Cruiné, "Increasing the Proportional Content of Surfactant (Cremophor EL Relative to Lipid in Self-emulsifying Lipid-based Formulations of Danazol Reduces Oral Bioavailability in Beagle Dogs," Pharm. Res., 24(4): 748-757 (2007).
Cruiné, et al., "Evaluation of the Impact of Surfactant Digestion on the Bioavailability of Danazol after Oral Administration of Lipidic Self-Emulsifying Formulations to Dogs," J. Pharm. Sci., 96(2): 995-1012, (2008).
Dahan, A. et al., Ch. 6: Enhanced Gastrointestinal Absorption of Lipophilic Drugs, Enhancement in Drug Delivery, (2006) pp. 111-131.
Dahan, et al., "Rationalizing the selection of oral lipid based drug delivery systems by an in vitro dynamic lipolysis model for improved oral bioavailability of poorly water soluble drugs," J. Cont. Rel., 129: 1-10 (2008).
Devani, et al., "The emulsification and solubilisation properties of polyglycolysed oils in self-emulsifying formulations," J. Pharm. Pharmacol., 56: 307-317 (2004).
Dressman, et al., "Dissolution testing as a prognostic tool for oral drug absorption: immediate release dosage forms.," Pharm. Res., 15: 11-22 (1998).
Dressman, et al., "In vitro-in vivo correlations for lipophilic, poorly water-soluble drugs," Eur J. Pharm. Sci., 11: S73-S80 (2000).
Erlich, et al., "Relative bioavailability of danazol in dogs from liquid-filled hard gelatin capsule" Int. J. Pharm,. 179 (1): 49-53 (1999).
Excerpt from GlaxoSmithKline's New Drug Application No. 21-319 for DUAGEN (Dutasteride): Summary Review of Pharmacokinetics and Bioavailability, pp. 13-19 (Oct. 5, 2001).
FDA, BCS Classification-Formulations Report entitled Intra-Agency Agreement Between the Eunice Kennedy Shriver National Institute of Child Health and Human Development (NICHD) and the U.S. Food and Drug Administration (FDA) Oral Formulations Platform—Report 1.
Gao, et al., "Development of supersaturatable selfemulsifying drug delivery system formulations for improving the oral absorption of poorly soluble drugs," Expert Opin. Drug Delivery, 3 (1: L97-110 (2006).
Gao, et al., "Design and Development of Supersaturatable Self-Emulsifying Drug Delivery Systems for Enhancing the Gastrointestinal Absorption of Poorly Soluble Drugs," pp. 303-328 in Oral Lipid-Based Formulations: Enhancing the bioavailbility of poorly watersoluble drugs, 1st ed.; Hauss, ed.; Informa Healthcare: New York, vol. 170 (2007).
Gao, et al., "Development of a supersaturable SEDDS (S-SEDDS) formulation of paclitaxel with improved oral bioavailability." J. Pharm. Sci., 92(12): 2386-2398 (2003).
Gershanik, et al., "Self-dispersing lipid formulations for improving oral absorption of lipophilic drugs," Eur. J. Pharm. Biopharm., 50(1): 179-188 (2000).

(56) References Cited

OTHER PUBLICATIONS

Gershkovich, et al., "Inhibition of Intestinal Absorption of Cholesterol by Surface-Modified Nanostructured Aluminosilicate Compounds," J. Pharm. Sci., 98: 2390-2400 (2009).
Ghosh, et al., "Design and development of microemulsion drug delivery system of acyclovir for improvement of oral bioavailability," AAPS Pharm.Sci.Tech., 7: E1-E6 (2006).
Gibson, "Lipid-Based Excipients for Oral Drug Delivery," pp. 33-62 in Oral Lipid-Based Formulations: Enhancing the bioavailbility of poorly water-soluble drugs, Hauss, ed., Informa Heathcare: New York, vol. 170 (2007).
GlaxoSmithKline, "An Evaluation of the Relative Bioavailability of the GI 198745 (Dutasteride) Soft Gelatin Capsule with Monodiglycerides of Caprylic/Capric Acid (MDC) in Healthy Adult Male Volunteers," Clinical Study Register for Study No. ARIA1004, pp. 1-4, downloaded from http://www.gskclinicalstudyregister.com/files2/917.pdf1109 (Jan. 2005).
GlaxoSmithKline, AVODARTTM (dutasteride) Soft Gelatin Capsules, Prescribing Information, NDA 21-319/S-008, pp. 1-18 (Aug. 2004).
Gooren, et al., "Androgen Replacement Therapy: Present and Future," Drugs, 64(17): 1861-1891 (2004).
Grove, et al., "Bioavailability of seocalcitol II: development and characterisation of self-microemulsifying drug delivery systems (SMEDDS) for oral administration containing mediumand long chain triglycerides," Eur J. Pharm. Sci., 28: 233-242 (2006).
Groves, et al., "The self-emulsifying action of mixed surfactants in oil," Acta Pharm. Suec., 13: 361-372 (1976).
Gursoy, et al., "Self-emulsifying drug delivery systems (SEDDS) for improved oral delivery of lipophilic drugs," Biomed. Pharmacother., 58: 173-182 (2004).
Haskell, et al., "Perspectives in Pharmaceutical Nanotechnology," AAPS Newsmagazine, Jan. 2012, pp. 16-23 (2012).
Hauss, et al., "Lipid-Based Delivery Systems for Improving the Bioavailability and Lymphatic Transport of a Poorly Water-Soluble LTB4 Inhibitor", J. Pharm. Sci., 87(2): 164-169 (1998).
Hengge, et al., "Double-blind, randomized, placebo-controlled phase III trial of oxymetholone for the treatment of HIV wasting," AIDS, 17(5): 699-710 (2003).
Hong, et al., "A new self-emulsifying formulation of itroconazole with improved dissolution and oral absorption," J. Control Release, 110: 332-338 (2006).
Humberstone, et al., "Lipid-based vehicles for the oral delivery of poorly water soluble drugs," Adv. Drug Deliv. Rev., 25: 103-128 (1997).
James, K. C. et al., "Solubilities of Testosterone Proprionate and Related Esters in Organic Solvents", Journal of Pharmaceutical Sciences, 65(5):656-9, (1976).
James, K.C. et al., "The solubilities of the lower testosterone esters, Journal of Pharmacy and Pharmacology", 20:709-14, (1968).
Jannin, et al., "Approaches for the development of solid and semi-solid lipid based formulations," Adv. Drug Deliv. Rev., 60: 734-74 (2008).
Julianto, et al., "Improved bioavailability of vitamin E with a self-emulsifying formulation, " Int. J. Pharm., 200(25): 53-57 (2000).
Kang, et al., "Development of self-microemulsifying drug delivery systems (SMEDDS) for oral bioavailability enhancement of simvastatin in beagle dogs," Int. J. Pharm., 274: 65-73 (2004).
Kaur, et al., "Nanomedicine: Trends and Perspectives on Technologies and Products," Chapter 7, pp. 95-107 in Advances in NanoTechnology and Applications, vol. 2, Center for Nanotechnology Education, Research and Applications (Centera), Sullivan University, College of Pharmacy, Louisville, KY (2010).
Kawakami, et al., "Micro emulsion formulation for enhanced absorption of poorly soluble drug I Prescription design," J. Controlled Rel., 81: 65-74 (2002).
Khoo, et al., "Formulation design and bioavailability assessment of lipidic self-emulsifying formulations of halofantrine," Int. J. Pharm,. 167 (1-2): 155-164 (1998).

Kim, et al., "Preparation and In Vitro Evaluation of Self-Microemulsifying Drug Delivery Systems Containing Idebenone," Drug Dev. Ind. Pharm., 26: 523-529 (2000).
Kincl, et al., "Increasing Intestinal Absorption of Drugs by Formulation," Arch. Pharm., 319: 615-624 (1986).
Köhn, et al., "A new oral testosterone undecanoate formulation," World J. Urol., 21:311-315 (2003).
Kommuru, et al., "Self-emulsifying drug delivery systems (SEDDS) of coenzyme Q10: formulation development and bioavailability assessment," Int. J. Pharm., 212: 233-246 (2001).
Kossena, et al., "Probing drug solubilization patterns in the gastrointestinal tract after administration of lipid-based delivery systems: A phase diagram approach," J. Pharm. Sci., 93: 332-348 (2004).
Kossena, et al., "Separation and characterization of the colloidal phases produced on digestion of common formulation lipids and assessment of their impact on the apparent solubility of selected poorly water-soluble drugs," J. Pharm. Sci., 92: 634-648 (2003).
Kostewicz, et al., "Predicting the precipitation of poorly soluble weak bases upon entry in the small intestine," J. Pharm. Pharmacol., 56: 43-51 (2004).
Koukonen, et al., "Drug Solubilization Behavior During in Vitro Digestion of Simple Triglyceride Lipid Solution Formulaions," Pharm. Res., 2 (2): 245-253 (2004).
Koukonen, et al., "Drug Solubilization Behavior During in Vitro Digestion of Suspension Formulations of Poorly Water-Soluble Drugs in Triglyceride Lipids," Pharm. Res., 21 (2): 254-260 (2004).
Kuehl, et al. "Formulation and In Vivo Evaluation of Chlorpropham (CIPC) Oral Formulations," J. Pharm. Sci., 97(12): 5222-5228 (2008).
Liang, et al., "Inhibition of steriod 5α-reductase by specific aliphatic unsaturated fatty acids," Biochem. J., 285: 557-562 (1992).
Liu, et al., "Research and development in drug innovation: reflections from the 2013 bioeconomy conference in China, lessons learned and future perspectives," Acta Pharmaceutica Sinica B., 4(2): 112-119 (2014).
Loper, et al., "Equivalence of a self-emulsifying drug delivery system (SEDDS) and soybean oil for oral delivery of a 5a-reductase inhibitor in rhesus monkeys," pp. 369-372 in Proc. Eur. Symp. Formulation of Poorly-available Drugs for Oral Absorption, Couvreur et al., eds., Editions de Sante: Paris (1996).
MacGregor, et al., "Lipolysis of oily formulations in the gastrointestinal tract," Adv. Drug Delivery Rev., 25: 33-46 (1996).
MacKenzie, et al., "Targeting Mitochondrial STAT3 with the Novel Phospho-Valproic Acid (MDC-1112) Inhibits Pancreatic Cancer Growth in Mice," PLoS One, 8(5): 1-11 (2013).
Mattheolabakis, et al., "Nanodelivery strategies in cancer chemotherapy: biological rationale and pharmaceutical perspectives," Nanomedicine, 7(10): 1577-1590 (2012).
Mattheolabakis, et al., "Pegylation Improves the Pharmacokinetics and Bioavailability of Small-Molecule Drugs Hydrolyzable by Esterases: A Study of Phospho-Ibuprofen," J. Pharmacol. Exp. Ther., 351: 61-66 (2014).
Mattheolabakis, et al., "Sterically Stabilized Liposomes Incorporating the Novel Anticancer Agent Phospho-Ibuprofen (MDC-917): Preparation, Characterization, and In Vitro/In Vivo Evaluation," Pharm. Res., 29: 1435-1443 (2012).
Miller, et al., "Targeted Intestinal Delivery of Supersaturated Itraconazole for Improved Oral Absorption," Pharm. Res., 25 (6): 1450-1459 (2008).
Mohsin, et al., "Design of Lipid-Based Formulations for Oral Administration of Poorly Water-Soluble Drugs: Precipitation of Drug after Dispersion of Formulations in Aqueous Solution," J. Pharm. Sci., 98(10): 3582-3595.
Muchow, et al., "Production and characterization of testosterone undecanoate-loaded NLC for oral bioavailability enhancement," Drug Dev. Ind. Pharm., 37(1): 8-14 (2011).
Muchow, M. et al., Testosterone undecanoate—increase of oral bioavailability by nanostructured lipid carriers (NLC), Journal of Pharmaceutical Technology & Drug Research (2013), pp. 1-10.
Müllertz, et al., "New perspectives on lipid and surfactant based drug delivery systems for oral delivery of poorly soluble drugs," J. Pharm. Pharmacol., 62: 1622-1636 (2010).

(56) References Cited

OTHER PUBLICATIONS

Nicolaides, et al., "Biorelevant dissolution testing to predict the plasma profile of lipophilic drugs after oral administration," Pharm. Res., 18: 380-388 (2001).
O'Driscoll, "Lipid-based formulations for intestinal lymphatic delivery," Eur. J. Pharm. Sci., 15: 405-415 (2002).
Porter, C. et al., "Lipid-Based Formulations for Oral Administration: Opportunities for Bioavailability Enhancement and Lipoprotein Targeting of Lipophilic Drugs", Journal of Receptor & Signal Transduction Research, 21(2&3):215-57, (2001).
Porter, et al., "Lipid based formulations: Exploring the link between in vitro Supersaturation and in vivo exposure," Bull. Tech. Gattefoss, 104: 61-69 (2011).
Porter, et al., "Lipids and lipid-based formulations: optimizing the oral delivery of lipophilic drugs," Nature Reviews Drug Discovery, 6: 231-248 (2007).
Porter, et al., "Lymphatic transport of halofantrine in the triple-cannulated anaesthetized rat model; effect of lipid vehicle digestion," J. Pharm. Sci., 85: 351-356 (1996).
Porter, et al., "Preface: Lipid-based systems for the enhanced delivery of poorly water soluble drugs," Adv. Drug Del. Rev., 60(6): 615-616 (2008).
Porter, et al., "Susceptibility to Lipase-Mediated Digestion Reduces the Oral Bioavailability of Danazol After Administration as a Medium-Chain Lipid-Based Microemulsion Formulation," Pharm. Res., 21(8): 1405-1412 (2004).
Porter, et al., "Uptake of drugs into the intestinal lymphatics after oral administration," Adv. Drug Deliv. Rev., 25(1):71-89, (1997).
Porter, et al., "Use of in vitro lipid digestion data to explain the in vivo performance of triglyceride based lipid formulations for the oral administration of poorly water-soluble drugs: Studies with Halofantrine," J. Pharm. Sci., 93: 1110-1121 (2004).
Pouton, "Self-emulsifying drug delivery systems: Assessment of the efficiency of emulsification," Int. J. Pharm., 27: 335-348 (1985).
Pouton, "Assessment of the efficiency of self-emulsifying formulations," J. Pharm. Pharmacol., 36: 51P (1984).
Pouton, "Effects of the inclusion of a model drug on the performance of self-emulsifying formulations," J. Pharm. Pharmacol., 37: 1P (1985).
Pouton, "Formulation of poorly watersoluble drugs for oral administration: Physicochemical and physiological issues and the lipid formulation classification system," Eur. J. Pharm. Sci., 29: 278-287 (2006).
Pouton, "Formulation of self-emulsifying drug delivery systems," Adv. Drug Del. Rev., 25(1): 47-58 (1997).
Pouton, "Lipid formulations for oral administration of drugs: non-emulsifying, self-emulsifying and 'self-microemulsifying' drug delivery systems," Eur. J. Pharm. Sci., 11(Suppl. 2): S93-S98 (2000).
Pouton, et al., "Key issues when formulating with lipids." Bull. Tech. Gattefosse, 92: 41-50 (1999).
Pouton, et al., "Self-emulsifying systems for oral delivery of drugs," Proc. Int. Symp. Control. Rel. Bioact. Mater., 14: 113-114 (1987).
Pouton, Ph.D. thesis, University of London, London, UK (1982).
Quan, et al., "Studies on Preparation and Absolute Bioavailability of a Self-Emulsifying System Containing Puerarin," Chem. Pharm. Bull., 55(5): 800-803 (2007).
Rajesh, et al., "Lipid Based Self-Emulsifying Drug Delivery System (SEDDS) for Poorly Water-Soluble Drugs: A Review," J. Global Pharma Tech., 2(3): 47-55 (2010).
Reddy, et al., "Review on self micro emulsifying drug delivery systems," Int. J. Res. Pharm. Sci., 2(3): 382-392 (2011).
Reddy, et al., "Lymphatic transport of orally administered drugs," Indian J. Exp. Biol., 40: 1097-1109 (2002).
Reymond, et al., In Vivo Model for Ciclosporin Intestinal Absorption in Lipid Vehicle,. Pharm.Res., (10): 677-679 (1988).
Robinson, "Semi-solid formulations for oral drug delivery," Bulletin Technique-Gattefosse, 89: 11-13 (1996).

Roth, M.Y. et al., Steady-state pharmacokinetics of oral testosterone undecanoate with concomitant inhibition of 5a-reductase by finasteride, International Journal of Andrology, (2001) vol. 34, No. 601, pp. 541-547.
Rytting, Erik et al. "Aqueous and cosolvent solubility data for drug-like organic compounds." The AAPS journal7A (2005): E78-E105.
Sek, et al., "Examination of the impact of a range of Pluronic surfactants on the in vitro solubilisation behaviour and oral bioavailability of lipidic formulations of atovaquone," J. Pharm. Pharmacol., 58: 809-820 (2006).
Shah, et al., "Self-emulsifying drug delivery systems (SEDDS) with polyglycolyzed glycerides for improving in vitro dissolution and oral absorption of lipophilic drugs," Int. J. Pharm., 106(1): 15-23 (1994).
Shen, et al., "Preparation and evaluation of self-microemulsifying drug delivery systems (SMEDDS) containing atorvastatin," J. Pharm. Pharmacol., 58: 1183-1191 (2006).
Sivak, et al., "Protonated nanostructured aluminosilicate (NSAS) reduces plasma cholesterol concentrations and atherosclerotic lesions in Apolipoprotein E deficient mice fed a high cholesterol and high fat diet," Lipids in Health and Disease, 8: 30-34 (2009).
Solomon, et al., "Inhibition of lipolysis of medium-chain triglycerides by non-ionic surfactants, a structure/activity study," pp. 437-438 in Formulation of Poorly Available Drugs for Oral Administration, Couvreur et al., eds., Editions de Sante, Paris, Couvreur (1996).
Stegemann, et al., "When poor solubility becomes an issue: From early stage to proof of concept," Eur. J. Pharma. Sci., 31(5): 249-261 (2007.
Strickley, "Currently marketed oral lipid-based dosage forms: drug products and excipients," pp. 1-31 in "Oral Lipid-Based Formulations: Enhancing the Bioavailability of Poorly Water-Soluble Drugs," Hauss, ed., New York: Informa Healthcare (2007).
Subramanian, et al., "Formulation design of self-emulsifying drug delivery systems for improved oral bioavailability of celecoxib," Biol. Pharm. Bull., 27: 1993-1999 (2004).
Sunesen, et al., "Effect of liquid volume and food intake on the absolute bioavailability of danazol, a poorly soluble drug," Eur. J. Pharm. Sci., 24: 297-303 (2005).
Swerdloff, et al., "Dihydrotestosterone: Biochemistry, Physiology, and Clinical Implications of Elevated Blood Levels," Endocr. Rev., 38(3): 220-254 (2017).
Swerdloff, et al., "Long-Term Pharmacokinetics of Transdermal Testosterone Gel in Hypogonadal Men," J. Clin. Endocrinol. & Metab., 85(12): 4500-4510 (2000).
Talegaonkar, "Microemulsions: A Novel Approach to Enhanced Drug Delivery," Recent Patents Drug Del. Form., 2: 238-257 (2008).
Tarr, et al., "Enhanced intestinal absorption of cyclosporine in rats through the reduction of emulsion droplet size," Pharm. Res., 6: 40-43 (1989).
Trull, et al., "Enhanced absorption of new oral cyclosporin microemulsion formulation, Neoral, in liver transplant recipients with external biliary diversion," Transplant. Proc., 26: 2977-2978 (1994).
Tuleu, et al., "Comparative bioavailability study in dogs of a self-emulsifying formulation of progesterone presented in a pellet and liquid form compared with an aqueous suspension of progesterone" J. Pharm. Sci., 93: 1495-1502 (2004).
Vertzoni, et al., "Dissolution media simulating the intralumenal composition of the small intestine: physiological issues and practical aspects," J. Pharm. Pharmacol., 56: 453-462 (2004).
Wakerly, "Self-emulsifying drug delivery systems based on nonionic surfactant-oil mixtures," Ph.D. thesis, University of Bath, Bath, UK (1989).
Wakerly, et al., "Evaluation of the self-emulsifying performance of a non-ionic surfactantvegetable oil mixture," J. Pharm. Pharmacol., 39: 6P (1987).
Wakerly, et al., "Self-emulsification of vegetable oil-nonionic surfactant mixtures: A proposed mechanism of action," Chapter 18, pp. 242-255, in Phenomena in Mixed Surfactant Systems, Scamehorn et al., eds., ACS Symp. Ser. 311, American Chemical Society (1986).

(56) References Cited

OTHER PUBLICATIONS

Wakerly, et al., "The effect of surfactant HLB on the self-emulsifying efficiency of non-ionic surfactant vegetable oil mixtures," J. Pharm. Pharmacol., 38: 2P (1986).
Wong, et al., "Carboxylesterases 1 and 2 Hydrolyze Phospho-Nonsteroidal Anti-Inflammatory Drugs: Relevance to Their Pharmacological Activity," J. Pharmacol. Exp. Therapeutics, 340(2): 422-432 (2012).
Xie, et al., "In Vitro and In Vivo Metabolic Studies of Phospho-aspirin (MDC-22)," Pharm. Res., 29: 3292-3301 (2012).
Xie, et al., "Regioselective oxidation of phospho-NSAIDs by human cytochrome P450 and flavin monooxygenase isoforms: implications for their pharmacokinetic properties and safety," Br. J. Pharmacol., 167: 222-232 (2012).
Yalkowsky, "Solubilization by Cosolvents," Chapter 6, pp. 236-320, in Solubility and Solubilization in Aqueous Media, American Chemical Society, Oxford Univ. Press: New York, NY (1999).
Yañez, et al., "Intestinal lymphatic transport for drug delivery," Adv. Drug Del. Rev., 63: 923-942 (2011).
Yap, et al., "Influence of lipolysis and droplet size on tocotrienol absorption from self-emulsifying formulations," Int. J. Pharm., 281 (2004): 67-78 (2004).
Zangerberg, et al., "Adynamic in vitro lipolysis model. II: evaluation of the model," Eur. J. Pharm. Sci., 14: 237-244 (2001).
Zhu, et al., "Phospho-Sulindac (OXT-328) Inhibits the Growth of Human Lung Cancer Xenografts in Mice: Enhanced Efficacy and Mitochondria Targeting by its Formulation in Solid Lipid Nanoparticles," Pharm. Res., 29: 3090-3101 (2012).
Zhu, et al., "Phosphosulindac (OXT-328) Selectively Targets Breast Cancer Stem Cells In Vitro and in Human Breast Cancer Xenografts," Stem Cells, 30: 2065-2075 (2012).
BCS Classification—Formulations Report entitled Intra-Agency Agreement Between the Eunice Kennedy Shriver National Institute of Child Health and Human Development (NICHD) and the U.S. Food and Drug Administration (FDA) Oral Formulations Platform—Report 1 as of Mar. 11, 2016.
Charman, et al., "Physicochemical and physiological mechanisms for the effects of food on drug absorption: the role of lipids and pH," J. Pharm.Sci., 86: 269-282 (1997).
Constantinides, "Self-Emulsifying Drug Delivery Formulations in the 21st Century: Challenges and Opportunities," Chapter 28, pp. 284-296, in Controlled Drug Delivery: Designing Technologies for the Future, Park et al., eds., ACS Symposium Series 752, American Chemical Society (2000).
Constantinides, et al., "Considerations and recommendations on traditional and non-traditional uses of excipients in oral drug products," AAPS Open, 2: 1-6 (2016).
Conway, A.J., et al. Randomized clinical trial of testosterone replacement therapy in hypogonadal men; International Journal of Andrology, 1988, vol. 11, pp. 247-264.
Gao, et al., "Development of supersaturatable selfemulsifying drug delivery system formulations for improving the oral absorption of poorly soluble drugs," Expert Opin. Drug Delivery, 3(1):97-110 (2006).
International Application No. PCT/US2010/030788; International Preliminary Report on Patentability, dated Oct. 16, 2012; 5 pages.
International Application No. PCT/US2010/030788; International Search Report and Written Opinion, dated Dec. 1, 2010; 8 pages.
International Application No. PCT/US2014/030308; International Preliminary Report on Patentability, dated Sep. 15, 2015; 4 pages.
International Application No. PCT/US2014/030308; Written Opinion of the International Search Authority, date of completion Aug. 4, 2014; 3 pages.
Lachance, S. et al., "Importance of Measuring Testosterone in Enzyme-Inhibited Plasma for Oral Testosterone Undecanoate Androgen Replacement Therapy Clinical Trials", Future Sci. OA, 10 pages, (2015).
Patel, et al., "A Self Micro Emulsifying Drug Delivery System (SMEDDS)," Int. J. Pharma. Sci. Rev. Res., 4(3): 29-35 (2010).
Porter, et al., "Enhancing intestinal drug solubilisation using lipid-based delivery systems," Adv. Drug Del. Rev., 60: 673-691 (2008).
Porter, et al., "In vitro assessment of oral lipid based formulations," Adv. Drug Deliv. Rev., 50: S127-S147 (2001).
Pouton, et al., "Formulation of lipid-based delivery systems for oral administration: Materials, methods and strategies," Adv. Drug Del. Rev., 60: 625-637 (2008).
Sek, et al., "Evaluation of the in-vitro digestion profiles of long and medium chain glycerides and the phase behaviour of their lipolytic products," J. Pharm. Pharmacol., 54: 29-41 (2002).
U.S. Appl. No. 12/758,770; Applicant Initiated Interview Summary dated Apr. 27, 2012; 3 pages.
U.S. Appl. No. 12/758,770; Applicant Initiated Interview Summary dated Mar. 7, 2013; 3 pages.
U.S. Appl. No. 12/758,770; Examiner Initiated Interview Summary dated Aug. 3, 2012; 5 pages.
U.S. Appl. No. 12/758,770; Examiner Initiated Interview Summary dated Mar. 21, 2013; 6 pages.
U.S. Appl. No. 12/758,770; Non-Final Office Action dated Feb. 1, 2013; 14 pages.
U.S. Appl. No. 12/758,770; Non-Final Office Action dated Mar. 26, 2012; 14 pages.
U.S. Appl. No. 12/758,770; Notice of Allowance dated Aug. 3, 2012; 10 pages.
U.S. Appl. No. 12/758,770; Notice of Allowance dated Mar. 21, 2013; 6 pages.
U.S. Appl. No. 13/584,958; Final Office Action dated Jan. 31, 2014; 4 pages.
U.S. Appl. No. 13/584,958; Non-Final Office Action dated Nov. 8, 2013; 9 pages.
U.S. Appl. No. 13/584,958; Notice of Allowance dated Apr. 14, 2014; 5 pages.
U.S. Appl. No. 14/216,240; Final Office Action dated Dec. 15, 2016; 14 pages.
U.S. Appl. No. 14/216,240; Final Office Action dated May 27, 2015; 13 pages.
U.S. Appl. No. 14/216,240; Non-Final Office Action dated Apr. 28, 2016; 13 pages.
U.S. Appl. No. 14/216,240; Non-Final Office Action dated Dec. 24, 2014; 11 pages.
U.S. Appl. No. 14/290,540; Final Office Action dated Jun. 17, 2016; 10 pages.
U.S. Appl. No. 14/290,540; Non-Final Office Action dated Sep. 17, 2015; 8 pages.
U.S. Appl. No. 15/381,430; Non-Final Office Action dated Feb. 27, 2018; 14 pages.
U.S. Appl. No. 15/381,430; Non-Final Office Action dated May 11, 2017; 13 pages.
U.S. Appl. No. 15/458,240; Non-Final Office Action dated Feb. 7, 2018; 13 pages.
De La Torre X. et al., Detection of testosterone esters in human plasma, Journal of Mass Spectrometry, 1995, vol. 30, pp. 1039-1404.
International Application No. PCT/US2018/033497; International Search Report and Written Opinion dated Aug. 9, 2018, 9 pages.
Lachance S et al., Importance of measuring testosterone in enzyme-inhibited plasma for oral testosterone undecanoate androgen replacement therapy clinical trials, Future Sci OA. Nov. 1, 2015;1(4), pp. 1-9.
U.S. Appl. No. 14/290,540; Final Office Action dated Sep. 21, 2018; 25 pages.
U.S. Appl. No. 15/984,028; Non-Final Office Action dated Sep. 7, 2018; 5 pages.
U.S. Appl. No. 16/360,583, filed Mar. 21, 2019; 125 pages.
U.S. Appl. No. 16/295,427; filed Mar. 7, 2019; 58 pages.

ORAL TESTOSTERONE ESTER FORMULATIONS AND METHODS OF TREATING TESTOSTERONE DEFICIENCY COMPRISING SAME

FIELD OF THE INVENTION

The present invention relates generally to oral formulations of testosterone esters for the treatment of testosterone deficiency. More particularly, the present invention relates to pharmaceutical composition comprising testosterone undecanoate (TU) with enhanced and extended absorption and pharmacokinetics.

BACKGROUND OF THE INVENTION

Testosterone (T) is a primary androgenic hormone produced in the interstitial cells of the testes and is responsible for normal growth, development and maintenance of male sex organs and secondary sex characteristics (e.g., deepening voice, muscular development, facial hair, etc.). Throughout adult life, testosterone is necessary for proper functioning of the testes and its accessory structures, prostate and seminal vesicle; for sense of well-being; and for maintenance of libido, erectile potency.

Testosterone deficiency—insufficient secretion of T characterized by low serum T concentrations—can give rise to medical conditions (e.g., hypogonadism) in males. Symptoms associated with male hypogonadism include impotence and decreased sexual desire, fatigue and loss of energy, mood depression, regression of secondary sexual characteristics, decreased muscle mass, and increased fat mass. Furthermore, hypogonadism in men is a risk factor for osteoporosis, metabolic syndrome, type II diabetes and cardiovascular disease.

Various testosterone replacement therapies are commercially available for the treatment of male hypogonadism. Pharmaceutical preparations include both testosterone and testosterone derivatives in the form of intramuscular injections, implants, oral tablets of alkylated T (e.g., methyltestosterone), topical gels, or topical patches. All of the current T therapies, however, fail to adequately provide an easy and clinically effective method of delivering T. For example, intramuscular injections are painful and are associated with significant fluctuations in serum T levels between doses; T patches are generally associated with levels of T in the lower range of normal (i.e., clinically ineffective) and often cause substantial skin irritation; and T gels have been associated with unsafe transfer of T from the user to women and children. As well, the sole "approved" oral T therapy, methyltestosterone, is associated with a significant occurrence of liver toxicity. Over time, therefore, the current methods of treating testosterone deficiency suffer from poor compliance and thus unsatisfactory treatment of men with low T.

Testosterone and its esters are poorly bioavailable—owing to extensive first pass intestinal and hepatic metabolism—or ineffective—due to an inability of the body to liberate testosterone from its testosterone prodrug. For example, testosterone and testosterone esters with side chains of less than 10 carbons in length are primarily absorbed via the portal circulation resulting in substantial, if not total, first pass metabolism. Fatty acid esters of long carbon chains (i.e., 14 or more carbons) may be absorbed by intestinal lymphatics, but the longer the fatty acid chain length, the slower the rate and extent of hydrolysis of the ester by esterases to liberate testosterone thus resulting in poor (i.e., clinically ineffective) pharmacological activity.

Other than selection of a testosterone ester, the formulation of the testosterone ester presents unique challenges. The gastrointestinal environment is decidedly aqueous in nature, which requires that drugs must be solubilzed for absorption. However, testosterone and particularly its esters are extremely insoluble in water and aqueous media, and even if the T or T ester is solubilized initially in the formulation, the formulation must be able to maintain the drug in a soluble or dispersed form without precipitation or, otherwise, coming out of solution in vivo (although such a property can be tested in vitro, for example, by mixing the contents of a formulation in simulated intestinal fluid). Furthermore, an oral T formulation must, effectively release T or T ester according to a desired release profile. Hence, an effective formulation of T or T ester must balance good solubility with optimum release and satisfaction of a targeted plasma or serum concentration profile.

For these reasons, among others, no oral formulation of testosterone or testosterone esters has been approved by the United States Food and Drug Administration (FDA) to date. In fact, the only oral testosterone product ever approved to date by the FDA is methyltestosterone (in which a methyl group covalently bound to a testosterone "nucleus" at the C-17 position to inhibit hepatic metabolism; note, also, that methyltestosterone is not a prodrug of testosterone) and this approval occurred several decades ago. Unfortunately, use of methyltestosterone has been associated with a significant incidence of liver toxicity, and it is rarely prescribed to treat men with low testosterone.

As noted above, fatty acid esters of testosterone provide yet another mode of potential delivery of testosterone to the body (i.e., as a "prodrug"). Once absorbed, testosterone can be liberated from its ester via the action of non-specific tissue and plasma esterases. Furthermore, by increasing the relative hydrophobicity of the testosterone moiety and the lipophilicity of the resulting molecule as determined by its n-octanol-water partition coefficient (log P) value, such prodrugs can be absorbed, at least partially, via the intestinal lymphatics, thus reducing first-pass metabolism by the liver. In general, lipophilic compounds having a log P value of at least 5 and oil solubility of at least 50 mg/mL are transported primarily via the lymphatic system.

Despite their promise, prodrugs of testosterone, including testosterone esters, have not been formulated in a manner to achieve effective and sustained serum testosterone levels at eugonadal levels (i.e., average serum T concentration falling in the range of about 300-1100 ng/dL). In fact, an orally administered pharmaceutical preparation of a testosterone prodrug, including testosterone esters, has yet to be approved by the FDA.

Hence, there remains a need for an oral formulation of a testosterone ester, which provides optimum serum testosterone levels that are clinically effective to treat hypogonadal men (i.e., those with a serum T concentration of ≤300 ng/dL) over an extended period of time.

SUMMARY OF THE INVENTION

In one embodiment of the present invention, an oral pharmaceutical composition is provided comprising testosterone undecanote solubilized in a carrier comprising at least one lipophilic surfactant and at least one hydrophilic surfactant in a total lipohilic surfactant to total hydrophilic surfactant ratio (w/w) falling in the range of about 6:1 to 3.5:1, which composition, upon once- or twice-daily oral administration, provides an average serum testosterone concentration at steady state falling in the range of about 300 to about 1100 ng/dL. The pharmaceutical composition provides a $C_{max}$ that, when administered with a meal, does not exceed 2500 ng/dL, preferably does not exceed 1800 ng/dL, and most preferably does not exceed 1500 ng/dL.

According to a preferred embodiment, the at least one hydrophilic surfactant comprises Cremophor RH 40 (polyoxyethyleneglycerol trihydroxystearate); the at least one lipophilic surfactant comprises oleic acid. The pharmaceutical compositions of the invention may comprise 18 to 22 percent by weight of the solubilized testosterone undecanoate, and may further be substantially free of a monohydric alcohols such as ethanol.

In another embodiment of the invention, a dosage form of testosterone undecanoate is provided comprising testosterone undecanote solubilized in a carrier comprising at least one lipophilic surfactant and at least one hydrophilic surfactant, which dosage form, upon once- or twice-daily oral administration to a subject suffering from hypogonadism or its symptoms, provides an average serum testosterone concentration at steady state falling in the range of about 300 to about 1100 ng/dL, while avoiding an occurrence of a $C_{max}$ value that exceeds 2500 ng/dL, more preferably avoiding an occurrence of a $C_{max}$ value that exceeds 1800 ng/dL, and most preferably avoiding an occurrence of a $C_{max}$ value that exceeds 1500 ng/dL.

In yet another embodiment of the present invention, a pharmaceutical composition is provided comprising testosterone undecanoate solubilized in a carrier comprising at least one lipophilic surfactant and at least one hydrophilic surfactant, which composition, upon oral administration with a meal having a fat content ranging from as low as 20 wt % to as high as 50 wt %, provides an average serum testosterone concentration that is statistically insignificant to that observed upon oral administration with a meal having a fat content of about 30 wt %.

In still yet another embodiment of the invention, a pharmaceutical composition is provided comprising testosterone undecanote solubilized in a carrier comprising at least one lipophilic surfactant and at least one hydrophilic surfactant in a total lipohilic surfactant to total hydrophilic surfactant ratio (w/w) falling in the range of about 6:1 to 3.5:1, which composition, upon once- or twice-daily oral administration, provides a serum testosterone rapid phase half-life of about 5 hours and a serum testosterone terminal high-life of about 29 hours.

In still yet another embodiment of the invention, a pharmaceutical composition is provided comprising testosterone undecanote solubilized in a carrier comprising at least one lipophilic surfactant and at least one hydrophilic surfactant in a total lipophilic surfactant to total hydrophilic surfactant ratio (w/w) falling in the range of about 6:1 to 3.5:1, which composition, upon once- or twice-daily oral administration to a subject suffering from testosterone deficiency or its symptoms, provides a mean serum testosterone concentration at day 30 of a daily treatment regimen, which is substantially the same as that observed on day 7. According to the invention, the mean serum testosterone concentration obtained at day 30 of a daily treatment regimen may also be substantially the same as that observed on day 60.

In another embodiment of the invention, a method of treating testosterone deficiency or its symptoms is provided comprising orally administering to a subject suffering from testosterone deficiency or its symptoms an effective amount of a pharmaceutical composition comprising testosterone undecanote solubilized in a carrier comprising at least one lipophilic surfactant and at least one hydrophilic surfactant in a total lipophilic surfactant to total hydrophilic surfactant ratio (w/w) falling in the range of about 6:1 to 3.5:1 to provide an average serum testosterone concentration at steady state falling in the range of about 300 to about 1100 ng/dL. The composition may be administered once daily or twice daily, and can give rise to a $C_{max}$ value falling in the range of about 900 to 1100 ng/dL.

According to the method, the composition may be administered with a meal comprising at least 20 wt % fat. The method can give rise to substantially no diurnal testosterone pharmacokinetic variation, an average serum $T_{max}$ value falling in the range of about 3 to 7 hours after oral administration, and substantially no significant decline in steady state serum testosterone response is observed upon repeat dosing.

In a preferred embodiment of the present invention, a pharmaceutical composition is provided comprising:
(a) 15-25 percent by weight of a solubilized testosterone undecanoate;
(b) 12-18 percent by weight of at least one hydrophilic surfactant;
(c) 50-65 percent by weight of at least one lipophilic surfactant;
(d) 10-15 percent by weight of a mixture of borage oil and peppermint oil,
which composition may be free of monohydric alcohols generally, specifically, ethanol and, upon oral administration to a subject in need thereof, gives rise to a serum testosterone half-life ($T_{1/2}$) falling in the range of about 10 hours to about 18 hours. Cremophor RH40 is a preferred hydrophilic surfactant and a preferred lipophilic surfactant is oleic acid. Borage oil and peppermint oil are both considered lipophilic surfactants.

In a particularly preferred embodiment, the composition comprises:
(a) 18-22 percent by weight of a solubilized testosterone undecanoate;
(b) 15-17 percent by weight of at least one hydrophilic surfactant;
(c) 50-55 percent by weight of at least one lipophilic surfactant; and;
(d) 10-15 percent by weight of a mixture of borage oil and peppermint oil.

The ratio of borage oil to peppermint oil may range from 8:1 to 3:1; preferably from 6:1 to 5:1; most preferably from 5:1 to 4:1. In addition, to Cremophor RH40, Solutol HS-15, Tween 80 and TPGS are preferred hydrophilic surfactants; and, in addition to oleic acid, Glycerol monoleate, propylene glycol laurate and Capmul MCM are preferred lipophilic surfactants. Combinations of two or more lipophilic surfactants and two or more hydrophilic surfactants are also contemplated.

In another embodiment of the present invention, a method of treating testosterone deficiency is provided, the method comprising orally administering to a hypogonadal subject an effective amount of a pharmaceutical composition comprising:
(a) 15-25 percent by weight of a solubilized testosterone undecanoate;
(b) 12-18 percent by weight of one or more hydrophilic surfactants;
(c) 50-65 percent by weight of one or more lipophilic surfactants;
(d) 10-15 percent by weight of a mixture of borage oil and peppermint oil, and free of ethanol, whose once- or twice-daily oral administration gives rise to an average (or a mean) steady state serum testosterone concentration, $C_{ave}$, falling in the range of about 300 and about 1100 ng/dL in the subject. The composition may optionally be administered with a meal whose fat content ranges from about 15 wt % to about 25 wt % or more. According to the method, any one or all of the following pharmacokinetic parameters may be achieved in the subject:

(a) serum testosterone $C_{max}$ within 900 and 1100 ng/dL in the subject;

(b) substantially no diurnal testosterone pharmacokinetic variation;

(c) serum $T_{max}$ 3 to 7 hours after administering the composition; and (d) substantially no decline in steady state serum testosterone response is observed upon repeat dosing.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other moieties, methods and systems for carrying out the several purposes of the present invention. For example, some embodiments of the invention may combine TU with other active drugs, including other hormones, in an oral delivery system that, in part, prevents or alleviates symptoms associated with testosterone deficiency. It is important, therefore, that the claims be regarded as including such equivalent constructions, which do not depart from the scope and spirit of the present invention.

DETAILED DESCRIPTION OF THE INVENTION

Figure 1:
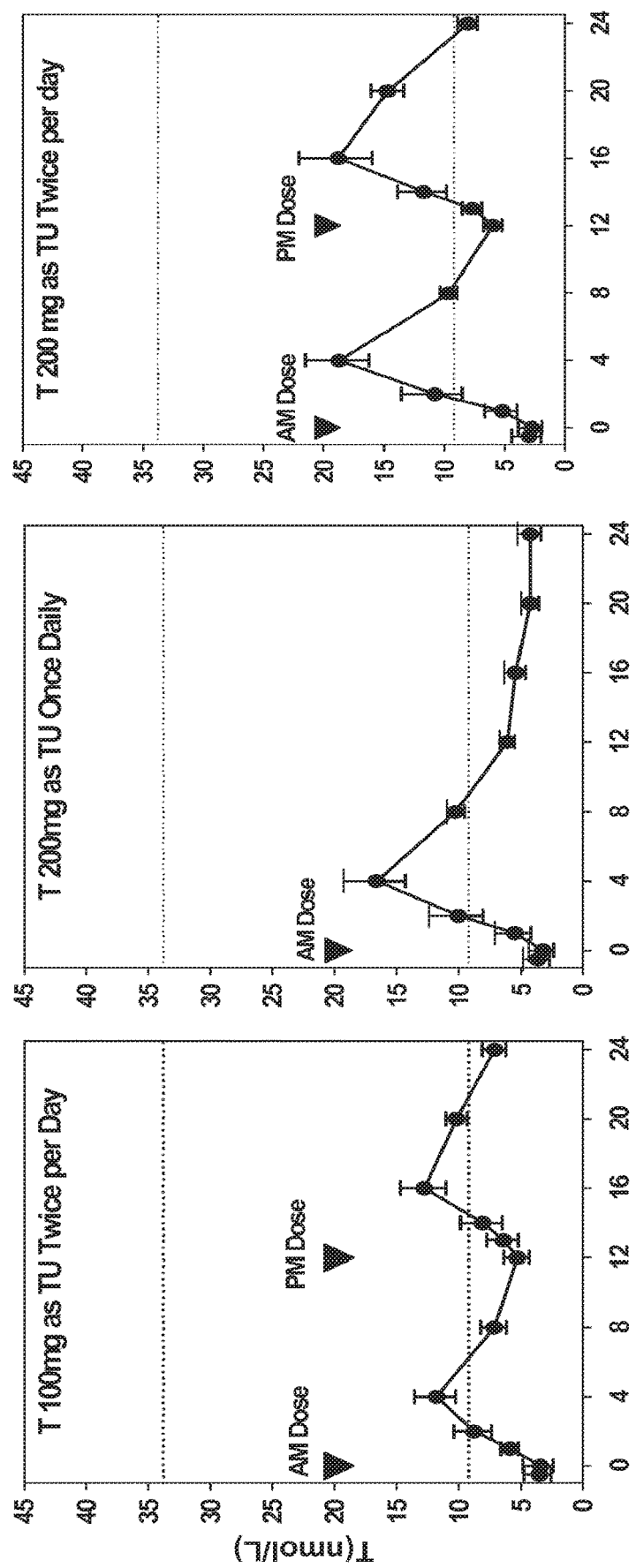
FIG. 1 provides serum T levels over a 24 hour period of once or twice daily oral dosing of a TU formulation of the invention.

The present invention provides an oral pharmaceutical composition comprising TU, which when administered no more than twice a day to hypogonadal males, provides average steady state serum levels (concentrations) of testosterone in such males, which fall within a desired "normal" or eugonadal range (i.e., about 300-1100 ng/dL) while avoiding the high $C_{max}$ values that are considered by the United States Food and Drug Administration to be undesirable, if not unacceptable. For instance FDA approval guidelines state that less than 85% of treated subjects may have a $C_{max}$ value of 1500 ng/dL or greater, and that none may have a $C_{max}$ value exceeding 2500 ng/dL. Less than 5% of treated subjects may have a $C_{max}$ value falling in the range of 1800-2500 ng/dL. Moreover, the formulations of the invention are designed to be self-emulsifying drug delivery systems (SEDDS) so that a TU-containing emulsion (or dispersion) is formed upon mixing with intestinal fluids in the gastrointestinal tract.

In one embodiment of the present invention, testosterone and/or esters at the C-17 position of the testosterone molecule, alone or in combination with other active ingredients, may be orally delivered using the inventive formulation. For example, the combination of testosterone undecanoate with an orally active inhibitor of Type I or Type II 5α-reductase or the combination of testosterone undecanoate with a synthetic progestin may be preferable in some embodiments.

While many of the embodiments of the present invention will be described and exemplified with the undecanoate acid ester of testosterone (i.e., TU), other esters of hydrophobic compounds, including T, can be adopted for oral delivery based on the teachings of the specification. In fact, it should be readily apparent to one of ordinary skill in the art from the teachings herein that the inventive drug delivery systems and compositions therefrom may be suitable for oral delivery of other testosterone esters, such as short-chain ($C_2$-$C_6$), medium-chain ($C_7$-$C_{13}$) and long-chain ($C_{14}$-$C_{24}$) fatty acid esters, preferably medium-chain fatty acid esters of testosterone.

The formulations of the present invention comprise a T-ester dissolved in a mixture comprising one or more lipophilic surfactants and one or more hydrophilic surfactants. A lipophilic surfactant as defined herein has a hydrophilic-lipophilic balance (HLB) value of less than 10, and preferably less than 5. A hydrophilic surfactant as defined herein has an HLB value of greater than 10. (HLB is an empirical expression for the relationship of the hydrophilic and hydrophobic groups of a surface active amphiphilic molecule, such as a surfactant. It is used to index surfactants and its value varies from about 1 to about 45 and includes both non-ionic and ionic surfactants. The higher the HLB, the more water soluble/dispersible the surfactant.)

According to one aspect of the present invention, each of the components of the delivery system (i.e., the lipophilic and hydrophilic surfactants) individually have solubilizing characteristics and contribute, in part, to solubilizing the active ingredient. Those lipophilic surfactants that contribute substantially to dissolving the drug are defined herein as "primary" solvent(s). It should be appreciated, however, that solubility can be affected by the temperature of the solvent/formulation. Formulations of the present invention comprising, for example, about 20% testosterone undecanoate, remain soluble at or above 30° C., including in the range of 30 to about 40° C.

A hydrophilic surfactant component may be necessary to achieve desirable dispersability of the formulation in the GI tract and release of the drug. That is, a hydrophilic surfactant, in addition to serving as a secondary solvent, may be required to release the drug from within the lipid carrier matrix, or primary solvent. In this respect, a high HLB surfactant, such as Cremophor RH40, can generally suffice. The levels (amounts) of the high HLB surfactant can be adjusted to provide optimum drug release without compromising the solubilization of the active ingredient.

Lipophilic surfactants suitable in drug delivery systems of the present invention include:

Fatty acids ($C_6$-$C_{24}$, preferably $C_{10}$-$C_{24}$, more preferably $C_{14}$-$C_{24}$), for example, octanoic acid, decanoic acid, undecanoic acid, lauric acid, myristic acid, palmitic acid, stearic acid, oleic acid, linoleic acid, and linolenic acid. Oleic acid is preferred.

Mono- and/or di-glycerides of fatty acids, such as Imwitor 988 (glyceryl mono-/di-caprylate), Imwitor 742 (glyceryl mono-/di-caprylate/caprate), Imwitor 308 (glyceryl mono-caprylate), Imwitor 191 (glyceryl mono-stearate), Softigen 701 (glyceryl mono-/di-ricinoleate), Capmul MCM (glyceryl mono-/di-caprylate/caprate), Capmul MCM(L) (liquid form of Capmul MCM), Capmul GMO (glyceryl mono-oleate), Capmul GDL (glyceryl dilaurate), Maisine (glyceryl mono-linoleate), Peceol (glyceryl mono-oleate), Myverol 18-92 (distilled monoglycerides from sunflower oil) and Myverol 18-06 (distilled monoglycerides from hydrogenated soybean oil), Precirol ATO 5 (glyceryl palmitostearate) and Gelucire 39/01 (semi-synthetic glycerides, i.e., $C_{12-18}$ mono-, di- and tri-glycerides). The preferred members of this class of lipophilic surfactants are the partial glycerides of oleic, palmitic and stearic acids and blends thereof.

Acetic, succinic, lactic, citric and/or tartaric esters of mono- and/or di-glycerides of fatty acids, for example, Myvacet 9-45 (distilled acetylated monoglycerides), Miglyol 829 (caprylic/capric diglyceryl succinate), Myverol SMG (mono/di-succinylated monoglycerides), Imwitor 370 (glyceryl stearate citrate), Imwitor 375 (glyceryl monostearate/citrate/lactate) and Crodatem T22 (diacetyl tartaric esters of monoglycerides).

Propylene glycol mono- and/or di-esters of fatty acids, for example, Lauroglycol (propylene glycol monolaurate), Mirpyl (propylene glycol monomyristate), Captex 200 (propylene glycol dicaprylate/dicaprate), Miglyol 840 (propylene glycol dicaprylate/dicaprate) and Neobee M-20 (propylene glycol dicaprylate/dicaprate).

Polyglycerol esters of fatty acids such as Plurol oleique (polyglyceryl oleate), Caprol ET (polyglyceryl mixed fatty acids) and Drewpol 10.10.10 (polyglyceryl oleate).

Castor oil ethoxylates of low ethoxylate content (HLB<10) such as Etocas 5 (5 moles of ethylene oxide reacted with 1 mole of castor oil) and Sandoxylate 5 (5 moles of ethylene oxide reacted with 1 mole of castor oil).

Acid and ester ethoxylates formed by reacting ethylene oxide with fatty acids or glycerol esters of fatty acids (HLB<10) such as Crodet 04 (polyoxyethylene (4) lauric acid), Cithrol 2MS (polyoxyethylene (2) stearic acid), Marlosol 183 (polyoxyethylene (3) stearic acid) and Marlowet G12DO (glyceryl 12 EO dioleate).

Sorbitan esters of fatty acids, for example, Span 20 (sorbitan monolaurate), Crill 1 (sorbitan monolaurate) and Crill 4 (sorbitan mono-oleate).

Transesterification products of natural or hydrogenated vegetable oil triglyceride and a polyalkylene polyol (HLB<10), e.g. Labrafil M1944CS (polyoxyethylated apricot kernel oil), Labrafil M2125CS (polyoxyethylated corn oil) and Gelucire 37/06 (polyoxyethylated hydrogenated coconut). Labrafil M1944CS is preferred.

Alcohol ethyoxylates (HLB<10), e.g. Volpo N3 (polyoxyethylated (3) oleyl ether), Brij 93 (polyoxyethylated (2) oleyl ether), Marlowet LA4 (polyoxyethylated (4) lauryl ether).

Pluronics, for example, Polyoxyethylene-polyoxypropylene co-polymers and block co-polymers (HLB<10) e.g. Synperonic PE L42 (HLB=8) and Synperonic PE L61 (HLB=3).

Mixtures of suitable lipophilic surfactants, such as those listed above, may be used if desired, and in some instances are found to be advantageous.

Any pharmaceutically acceptable hydrophilic surfactant (i.e., having an HLB value greater than 10) may be used in the present invention. Some non-limiting examples include:

Castor oil or hydrogenated castor oil ethoxylates (HLB>10), e.g. Cremophor EL (polyoxyethylene (35) castor oil), Cremophor RH40 (polyoxyethylene (40) hydrogenated castor oil), Etocas 40 (polyoxyethylene (40) castor oil), Nikkol HCO-60 (polyoxyethylene (60) hydrogenated castor oil), Solutol HS-15 (polyethylene glycol 660 hydroxystearate), Labrasol (caprylocaproyl macrogol-8 glycerides), α-tocopherol-polyethylene glycol-1000-succinate (TPGS) and ascorbyl-6 palmitate. Cremophor RH40 is preferred.

Polyoxyethylene sorbitan fatty acid derivates, e.g. Tween 20 (polyoxyethylene (20) monolaureate), Tween 80 (polyoxyethylene (20) monooleate), Crillet 4 (polyoxyethylene (20) monooleate) and Montanox 40 (polyoxyethylene (20) monopalmitate). Tween 80 (Polysorbate 80) is preferred.

Gelucires, preferably Gelucire 50/13 (PEG mono- and diesters of palmitic and stearic acids. (In reference to Gelucires, the first number (i.e., 50) corresponds to the melting point of the material and the second (i.e., 13) to the HLB number.)

Fatty acid ethoxylates (HLB>10), e.g. Myrj 45 (polyoxyethylene (8) stearate), Tagat L (polyoxyethylene (30) monolaurate), Marlosol 1820 (polyoxyethylene (20) stearate) and Marlosol OL15 (polyoxyethylene (15) oleate). Myrj 45 is preferred.

Alcohol ethoxylates (HLB>10), e.g. Brij 96 (polyoxyethylene (10) oleyl ether), Volpo 015 (polyoxyethylene (15) oleyl ether), Mario wet OA30 (polyoxyethylene (30) oleyl ether) and Marlowet LMA20 (polyoxyethylene (20) $C_{12}$-$C_{14}$ fatty ether).

Polyoxyethylene-polyoxypropylene co-polymers and block co-polymers (HLB>10), that are commercially available under the trade name Pluronics or Poloxamers, such as Poloxamers 188 and 407 also known as Syperonic PE L44 (HLB=16) and Syperonic F127 (HLB=22), respectively.

Anionic surfactants, e.g. sodium lauryl sulphate, sodium oleate and sodium dioctylsulphosuccinate.

Alkylphenol surfactants (HLB>10), e.g. Triton N-101 (polyoxyethylene (9-10) nonylphenol) and Synperonic NP9 (polyoxyethylene (9) nonylphenol).

As mentioned, in one aspect of the present invention, each of the components of the delivery system (i.e., the lipophilic and hydrophilic surfactants) individually has solvent characteristics and contributes, in part, to solubilizing the active ingredient. In this way, without being bound by or limited to theory, the present invention does not require additional solvents, such as cosolvents, but these may be optionally included in the inventive systems and formulations.

Optional cosolvents suitable with the instant invention are, for example, water, short chain mono-, di-, and polyhydric alcohols, such as ethanol, benzyl alcohol, glycerol, propylene glycol, propylene carbonate, polyethylene glycol with an average molecular weight of about 200 to about 10,000, diethylene glycol monoethyl ether (e.g., Transcutol HP), and combinations thereof. Preferably, such cosolvents, especially ethanol or other monoethanols, are excluded altogether.

Additional oils that may be incorporated in embodiments of the present invention include complete glycerol triesters of medium chain ($C_7$-$C_{13}$) or long chain ($C_{14}$-$C_{22}$) fatty acids with low molecular weight (up to $C_6$) mono-, di- or polyhydric alcohols. Some examples of oils for use in this invention thus include: vegetable oils (e.g., soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond, borage, peppermint and apricot kernel oils) and animal oils (e.g., fish liver oil, shark oil and mink oil).

In other embodiments of the present invention, methods and compositions for modulating (i.e., sustaining) the rate of available serum testosterone by incorporating component(s) that may biochemically modulate (1) TU absorption, (2) TU metabolism to T, and/or (3) metabolism of T to dihydrotestosterone (DHT). For example, the inclusion of medium to long chain fatty acid esters can enhance TU absorption. In this way, more TU may stave off hydrolysis in the gut and enter the blood stream. In other words, the fatty acid ester may competitively inhibit esterases that would otherwise metabolize TU. Examples of other esters or combinations thereof include botanical extracts or benign esters used as food additives (e.g., propylparben, octylacetate and ethylacetate).

Other components that can modulate TU absorption include "natural" and synthetic inhibitors of 5α-reductase, which is an enzyme present in enterocytes and other tissues that catalyzes the conversion of T to DHT. Complete or partial inhibition of this conversion may both increase and sustain increases serum levels of T after oral dosing with TU while concomitantly reducing serum DHT levels. Borage oil, which contains a significant amount of the 5α-reductase inhibitor, gamma-linolenic acid (GLA), is an example of a "natural" modulator of TU metabolism. Other than within borage oil, of course, GLA could be added directly as a separate component of a TU formulation of the invention. Many natural inhibitors of 5α-reductase are known in the art (e.g., epigallocatechin gallate, a catechin derived primarily from green tea and saw palmetto extract from berries of the *Serenoa repens* species), all of which may be suitable in the present invention. Non-limiting examples of synthetic 5α-reductase inhibitors suitable for use in the present invention include compounds such as finasteride, dutasteride and the like.

In addition to 5α-reductase inhibitors, the present invention contemplates the use of inhibitors of T metabolism via other mechanisms. One such point of inhibition may be the cytochrome P450 isozyme CYP3A4, which is present in enterocytes and in liver cells and thus capable of metabolizing testosterone. Accordingly, selected embodiments of the invention, include peppermint oil, which is known to contain components capable of inhibiting CYP3A4 activity.

Yet other optional ingredients which may be included in the compositions of the present invention are those which are conventionally used in oil-based drug delivery systems, e.g., antioxidants such as tocopherol, tocopherol acetate, ascorbic acid, butylhydroxytoluene (BHT), ascorbyl palmitate, butylhydroxyanisole and propyl gallate; pH stabilizers such as citric acid, tartaric acid, fumaric acid, acetic acid, glycine, arginine, lysine and potassium hydrogen phosphate; thickeners/suspending agents such as hydrogenated vegetable oils, beeswax, colloidal silicon dioxide, mannitol, gums, celluloses, silicates, bentonite; flavoring agents such as cherry, lemon and aniseed flavors; sweeteners such as aspartame, acesulfane K, sucralose, saccharin and cyclamates; etc.

The present inventors have learned that relative proportions of the one or more lipophilic surfactants and one or more hydrophilic surfactants can be critical to achieving the desired pharmacokinetics of the present invention. More specifically, the inventors have discovered a ratio of total lipophilic surfactant and total hydrophilic surfactant, which is not only able to solubilize a relatively large amount of T-ester (e.g., greater than 15%, 18%, 20%, 22%, or 25%) but one that is also able to provide optimum release of the T-ester from within the formulation. Preferably, the total oil (e.g., oleic acid+borage oil+peppermint oil, all of which are considered lipophilic surfactants) to hydrophilic surfactant ratio (w/w) falls in the range of about 6:1 to 1:1, 6:1 to 3.1, 6:1 to 3.5:1, or 6:1 to 4:1; and more preferably, from about 5:1 to 3:1, and most preferably, from about 4:1 to 3:1.

The following relative concentrations, by weight, are preferred (the percentages are based on the total weight of the formulation):

Hydrophilic surfactant: 10-20%, more preferably 12-18%, and most preferably 15-17%.

Lipophilic surfactant: 50-70%, more preferably 50-65%, and most preferably 50-55%

Other oils: 5-15%, more preferably 7-15%, and most preferably 10-13%

Drug: 10-30%, more preferably 15-25%, and most preferably 18-22%.

The formulations of the present invention have self-emulsifying properties, forming a fine emulsion upon dilution with aqueous media or intestinal fluids in vivo. In other words, the formulations may have high surfactant and lipid content designed for optimum dispersion upon mixing with an aqueous medium. Qualitative description of the self-emulsification property of the inventive formulations can be visually observed during the dissolution of same in vitro. On the other hand, quantitative measurements may be taken of the particle size of the emulsified droplets using laser light scattering and/or turbidity measurements in the dissolution medium by UV/VIS spectrophotometer. Any of these methodologies are available and known to one of ordinary skill in the art.

The pharmaceutical compositions according to the present invention are preferably liquid or semi-solid at ambient temperatures. Furthermore, these pharmaceutical compositions can be transformed into solid dosage forms through adsorption onto solid carrier particles, such as silicon dioxide, calcium silicate or magnesium aluminometasilicate to obtain free-flowing powders which can be either filled into hard capsules or compressed into tablets. See, e.g., US 2003/0072798, the disclosure of which is incorporated in its entirety by reference. Hence, the term "solubilized" herein, should be interpreted to describe an active pharmaceutical ingredient (API), which is dissolved in a liquid solution or which is uniformly dispersed in a solid carrier. Also sachet type dosage forms can be formed and used.

The instant invention preferably comprises an API that is solubilized in the presence of lipid surfactant excipients (e.g., any combination of the lipophilic and hydrophilic surfactants noted above). Accordingly, the melting point of the surfactants used is one factor that can determine whether the resulting composition will be liquid or semi-solid at ambient temperature. Particularly preferred compositions of the present invention are liquid oral unit dosage forms, more preferably filled into hard or soft capsules, e.g. gelatin or non-gelatin capsules such as those made of cellulose, carrageenan, or pollulan. The technology for encapsulating lipid-based pharmaceutical preparations is well known to one of ordinary skill in the art. As the inventive delivery systems and formulations described herein are not limited to any one encapsulation method, specific encapsulation techniques need not be discussed further.

The drug carrier systems and pharmaceutical preparations according to the present invention may be prepared by conventional techniques for lipid-based drug carrier systems. In a typical procedure for the preparation of the preferred carrier systems of this invention, a lipophilic surfactant component is weighed out into a suitable stainless steel vessel and a hydrophilic surfactant component is then weighed and added to the container along with any additional components. In a preferred method, the hydrophobic drug may be first added to a lipophilic surfactant component (e.g., oleic acid) and completely dissolved before adding a hydrophilic surfactant component. In any case, mixing of the components may be effected by use of a homogenizing mixer or other high shear device and high temperature particularly when high melting point surfactants are used to ensure that all components are in homogenous liquid state before or after the addition of the drug.

In a situation in which a hydrophobic drug is weighed and added to a combined lipid mixture, mixing is continued, preferably at high temperature, until a homogenous solution is prepared. The formulation may be de-aerated before encapsulation in either soft or hard capsules. In some instances the fill formulation may be held at elevated temperature using a suitable jacketed vessel to aid processing. Also, in some instances, the homogenous solution may be filtered (e.g., through a 5 micron filter) before filling into capsules.

ovary and adrenal gland, but the amount is about one-tenth that observed in eugonadal men. The majority (≥98%) of circulating testosterone is bound to sex hormone binding globulin and albumin and is biologically active only when released in the free form. The term "free" is thus defined as not being bound to or confined within, for example, biomolecules, cells and/or lipid matrices of the inventive formulations described herein. Generally, "free" medicaments described herein refer to medicament that is accessible to metabolic enzymes circulating in serum.

While the present invention should not be limited to the delivery of testosterone or any particular ester thereof, TU has been found to offer unique chemical and physical characteristics that make its use preferable in some embodiments. The present inventors have learned that the undecanoate acid ester of testosterone, in particular, can yield superior bioavailability to that found with other equivalent esters (e.g., testosterone enanthate (TE)).

What is more, the use of TU in the formulations of the present invention is associated with a substantially lower serum DHT to T ratio than has been reported for other forms of T replacement—including oral formulations of TU (Table 1). Testosterone interacts with androgen receptors either directly or following its conversion to DHT via the action of 5α-reductase. DHT is a more potent androgen than testosterone and its elevated levels are thought by some scientists to increase the risk of prostate cancer. In this way, the present invention provides yet another unexpected advantage over other known testosterone delivery vehicles.

TABLE 1

Comparison of Serum DHT and DHT:T Ratios Observed in Response to T-Replacement by Various Routes of Administration

| Form of Androgen Replacement/Dose | Length of Exposure | Avg. Serum DHT (ng/dL) | Avg. DHT:T Ratio | Multiple of Clarus DHT:T Ratio | Reference |
|---|---|---|---|---|---|
| Oral TU in SEDDS [200 mg T (as TU), BID] | 7-Days | 107 | 0.24 | 1 | |
| Oral TU in SEDDS [200 mg T (as TU), BID] | 30-Days | 109 | 0.25 | 1 | |
| Scrotal T-Patch (4-6 mg, QD) (Testoderm ®) | 8 years | 175 | 0.42 | 1.75 | Atkinson et al (1998)[1] |
| Transdermal T-Gel (5-10 g, QD) (AndroGel ®) | 3 years | 130-210 | 0.25-0.30 | 1-1.25 | Swerdloff et al (2000)[2], Wang et al (2004)[3] |
| Oral TU (Andriol) [50 mg T (as TU), BID] | Several Months | 93 | 0.40 | 1.7 | Houwing et al (2003)[4] |
| Oral TU (Andriol) [50 mg T (as TU), BID] | 10 years | 90 | 0.50 | 2.1 | Gooren et al (1994)[5] |

[1] Atkinson, L E, Chang, Y-L and Synder, P J. (1998) Long-term experience with testosterone replacement through scrotal skin. In: *Testosterone: Action, Deficiency and Substitution* (Nieschlag, E and Behre, H M, eds). Springer-Verlag, Berlin, pp. 365-388
[2] Swerdloff, R S, et a (2000). Long-term pharmacokinetics of transdermal testosterone gel in hypogonadal men. *J. Clin. Endocrinol. Metab.* 85: 4500-4510.
[3] Wang, C et al (2004). Long-term testosterone gel (AndroGel ®) treatment maintains beneficial effects on sexual function and mood, lean and fat mass and bone mineral density in hypogonadal men. *J. Clin. Endocrinol. Metab.* 89: 2085-2098.
[4] Houwing, N S et al (2003). Pharmacokinetic study in women of three different doses of a new formulation of oral testosterone undecanoate, Andriol Testocaps. *Pharmcotherapy.* 23: 1257-1265.
[5] Gooren, L J G (1994). A ten-year safety study of the oral androgen testosterone undecanoate. *J. Androl.* 15: 212-215.

Returning now to the delivery of testosterone, the pharmaceutical compositions of the present invention may be suitable for testosterone therapy. Testosterone is the main endogenous androgen in men. Leydig cells in the testes produce approximately 7 mg of testosterone each day resulting in serum concentrations ranging from about 300 to about 1100 ng/dL. Women also synthesize testosterone in both the Specific embodiments of the instant invention will now be described in non-limiting examples. Table 2 provides composition details of various formulations of TU, in accordance with the teachings of the instant invention. For calculation purposes, 1 mg of T is equivalent to 1.58 mg T-undecanoate.

The compositions details of Table 2 (mg/capsule and wt. percentage) are based on an approximate fill weight of 800 mg fill weight per '00' hard gelatin capsule. However, at testosterone-ester amounts less than about 100 mg/capsule, the formulations may be proportionally adjusted for smaller total fill weights that would permit use of smaller hard gelatin capsules (e.g., size '0' or smaller size if needed).

As well, it should be apparent to one of ordinary skill in the art that many, if not all, of the surfactants within a category (e.g., lipophilic, hydrophilic, etc.) may be exchanged with another surfactant from the same category. Thus, while Table 1 lists formulations comprising oleic acid, one of ordinary skill in the art should recognize other lipophilic surfactants (e.g., those listed above) may be suitable as well. Similarly, while Table 1 lists formulations comprising Cremophor RH40 (HLB=13), one of ordinary skill in the art should recognize other hydrophilic surfactants (e.g., those listed above) may be suitable. Borage oil, peppermint oil, BHT, and ascorbyl palmitate may be substituted for chemically similar substances or eliminated.

TABLE 2

| | | | Composition % w/w (mg/"00" capsule)[1] | | | | | Fill |
|---|---|---|---|---|---|---|---|---|
| F. | TU | Oleic Acid | Cremophor RH40 | Borage Oil | Peppermint Oil | BHT | Ascorbyl Palmitate | Wt. (mg)[2] |
| 1 | 20 (158) | 51.5 (413) | 16 (128.5) | 10 (80) | 2.5 (20) | 0.06 (0.5) | — | 800 |
| 2 | 15 (120) | 54.5 (436) | 18 (144) | 10 (80) | 2.5 (20) | 0.02 (0.2) | 0.8 (6.4) | 806.6 |
| 3 | 17 (136) | 52.5 (420) | 18 (144) | 10 (80) | 2.5 (20) | 0.02 (0.2) | 0.8 (6.4) | 806.6 |
| 4 | 19 (152) | 50.5 (404) | 18 (144) | 10 (80) | 2.5 (20) | 0.02 (0.2) | 0.8 (6.4) | 806.6 |
| 5 | 21 (168) | 50 (400) | 16.5 (132) | 10 (80) | 2.5 (20) | 0.02 (0.2) | 0.8 (6.4) | 806.6 |
| 6 | 23 (184) | 50 (400) | 14.5 (116) | 10 (80) | 2.5 (20) | 0.02 (0.2) | 0.8 (6.4) | 806.6 |
| 7 | 25 (200) | 50 (400) | 12.5 (100) | 10 (80) | 2.5 (20) | 0.02 (0.2) | 0.8 (6.4) | 806.6 |
| 8 | 16 (128) | 53.5 (428) | 18 (144) | 10 (80) | 2.5 (20) | 0.02 (0.2) | 0.8 (6.4) | 806.6 |
| 9 | 18 (144) | 51.5 (413) | 18 (144) | 10 (80) | 2.5 (20) | 0.02 (0.2) | 0.8 (6.4) | 806.6 |
| 10 | 22 (176) | 50 (400) | 15.5 (124) | 10 (80) | 2.5 (20) | 0.02 (0.2) | 0.8 (6.4) | 806.6 |
| 11 | 24 (192) | 50 (400) | 13.5 (108) | 10 (80) | 2.5 (20) | 0.02 (0.2) | 0.8 (6.4) | 806.6 |
| 12 | 15 (120) | 55.5 (444) | 17 (136) | 10 (80) | 2.5 (20) | 0.02 (0.2) | 0.8 (6.4) | 806.6 |
| 13 | 17 (136) | 53.5 (428) | 17 (136) | 10 (80) | 2.5 (20) | 0.02 (0.2) | 0.8 (6.4) | 806.6 |
| 14 | 19 (152) | 51.5 (412) | 17 (136) | 10 (80) | 2.5 (20) | 0.02 (0.2) | 0.8 (6.4) | 806.6 |
| 15 | 15 (120) | 56.5 (452) | 16 (128) | 10 (80) | 2.5 (20) | 0.02 (0.2) | 0.8 (6.4) | 806.6 |
| 16 | 17 (136) | 54.5 (436) | 16 (128) | 10 (80) | 2.5 (20) | 0.02 (0.2) | 0.8 (6.4) | 806.6 |
| 17 | 19 (152) | 52.5 (420) | 16 (128) | 10 (80) | 2.5 (20) | 0.02 (0.2) | 0.8 (6.4) | 806.6 |
| 18 | 21 (168) | 50.5 (404) | 16 (128) | 10 (80) | 2.5 (20) | 0.02 (0.2) | 0.8 (6.4) | 806.6 |
| 19 | 20 (160) | 50.5 (404) | 17 (136) | 10 (80) | 2.5 (20) | 0.02 (0.2) | 0.8 (6.4) | 806.6 |
| 20 | 20 (160) | 51.5 (412) | 16 (128) | 10 (80) | 2.5 (20) | 0.02 (0.2) | 0.8 (6.4) | 806.6 |
| 21 | 15 (120) | 57.5 (460) | 15 (120) | 10 (80) | 2.5 (20) | 0.02 (0.2) | 0.8 (6.4) | 806.6 |
| 22 | 16 (128) | 56.5 (452) | 15 (120) | 10 (80) | 2.5 (20) | 0.02 (0.2) | 0.8 (6.4) | 806.6 |
| 23 | 17 (136) | 55.5 (444) | 15 (120) | 10 (80) | 2.5 (20) | 0.02 (0.2) | 0.8 (6.4) | 806.6 |
| 24 | 18 (144) | (54.5 (436) | 15 (120) | 10 (80) | 2.5 (20) | 0.02 (0.2) | 0.8 (6.4) | 806.6 |
| 25 | 19 (152) | 53.5 (428) | 15 (120) | 10 (80) | 2.5 (20) | 0.02 (0.2) | 0.8 (6.4) | 806.6 |
| 26 | 20 (158) | 51.5 (413) | 16 (128.5) | 9.4 (75) | 3.1 (25) | 0.06 (0.5) | — | 800 |
| 27 | 20 (158) | 51.5 (413) | 16 (128.5) | 10.6 (85) | 1.9 (15) | 0.06 (0.5) | — | 800 |
| 28 | 20 (158) | 51.5 (413) | 16 (128.5) | 11.2 (90) | 1.2 (10) | 0.02 (0.2) | 0.8 (6.4) | 806.1 |
| 29 | 20 (158) | 51.5 (413) | 16 (128.5 | 11.8 (95) | 0.6 (5) | 0.02 (0.2) | 0.8 (6.4) | 806.1 |
| 30 | 25 (200) | 50 (400) | 12.5 (100) | 10.6 (85) | 1.9 (15) | 0.06 (0.5) | — | 800.5 |

[1]Milligram weights rounded to nearest whole number; 800 (±10%)
[2]±8 mg

Preferred formulations of TU filled into size "00" capsules in accordance with the present invention are:

Formulation A

| Ingredients | mg/capsule | %, w/w |
|---|---|---|
| Testosterone Undecanoate | 158.3 | 19.8 |
| Oleic Acid | 413.1 | 51.6 |
| Cremophor RH 40 | 128.4 | 16.1 |
| Borage Seed Oil | 80.0 | 10 |
| Peppermint Oil | 20.0 | 2.5 |
| BHT | 0.2 | 0.03 |
| Total | 800 | 100 |

Formulation B

| Ingredients | mg/capsule | %, w/w |
|---|---|---|
| Testosterone Undecanoate | 158.3 | 19.8 |
| Oleic Acid | 412.5 | 51.6 |
| Cremophor RH 40 | 128.4 | 16.0 |
| Peppermint Oil | 20.0 | 2.5 |
| Borage Seed Oil + 0.03% BHT | 80.0 | 10 |
| Ascorbyl Palmitate | 0.8 | 0.1 |
| Total | 800 | 100 |

In vivo and in vitro performance data of the formulations in keeping with the invention will next be described. However, the scope of the invention should not be limited to the following examples nor the specific formulations studied in the examples.

Example 1—Single-Day Study

Formulation B was studied for its single-day pharmacokinetic profile upon once- or twice-daily administration to hypogonadal men. The study was designed as an open-label, single-day dosing, sequential, cross-over, pharmakokinetic study. Twelve (12) hypogonadal men were enrolled after giving written informed consent, and all 12 subjects completed the study. Each subject received a daily dose of Formulation B as follows:

1. 200 mg T (as TU) QD, i.e., 2 capsules/dose
2. 200 mg T (as TU) BID (100 mg/dose), i.e., 1 capsule/dose
3. 400 mg T (as TU) BID (200 mg/dose)

The doses were administered as capsules to subjects five minutes after a meal (breakfast for QD, and breakfast and dinner for BID).

Table 3 provides the relevant PK parameters from the study:

TABLE 3

Single-Day Pharmacokinetic Parameters for T, DHT, and DHT:T Ratio

| Pharmacokinetic Parameter (unit) | Means (Standard Deviations) of Pharmacokinetic Parameters[a] | | |
|---|---|---|---|
| | Regimen 1 (TU QD 200 mg[b]) | Regimen 2 (TU BID 100 mg[b]) | Regimen 3 (TU BID 200 mg[b]) |
| T | | | |
| $AUC_{24}$ (ng · hr/dL) | 5907 (1840) | 6751 (2145) | 9252 (3173) |
| $C_{avg}$ (ng/dL) | 246 (77) | 281 (89) | 385 (132) |
| $T_{1/2}$ (hr)[a] | 15.5 (7.0-24.0) | 15.1 (4.5-43.4) | 8.0 (4.2-16.3) |
| $C_{max}$ (ng/dL) | 0-24 hrs: 557 (252) | 0-12 hrs: 470 (247) <br> 12-24 hrs: 466 (160) | 0-12 hrs: 626 (267) <br> 12-24 hrs: 718 (333) |
| $T_{max}$ (hr)[a] | 0-24 hrs: 4.0 (2.0-8.0) | 0-12 hrs: 4.0 (2.0-12.0) <br> 12-24 hrs: 16.0 (14.0-20.0) | 0-12 hrs: 4.0 (2.0-12.0) <br> 12-24 hrs: 16.0 (14.0-20.0) |
| DHT | | | |
| $AUC_{24}$ (ng · hr/dL) | 1097 (387) | 1400 (758) | 1732 (859) |
| $C_{avg}$ (ng/dL) | 45.7 (16.1) | 58.3 (31.6) | 72.2 (35.8) |
| $C_{max}$ (ng/dL) | 0-24 hrs: 122 (66) | 0-12 hrs: 81.3 (40.3) <br> 12-24 hrs: 97.9 (51.2) | 0-12 hrs: 108 (59) <br> 12-24 hrs: 114 (58) |
| $T_{max}$ (hr)[a] | 0-24 hrs: 4.0 (1.0-8.0) | 0-12 hrs: 4.0 (1.0-12.0) <br> 12-24 hrs: 16.0 (13.0-20.0) | 0-12 hrs: 4.0 (1.0-12.0) <br> 12-24 hrs: 16.0 (14.0-20.0) |
| DHT:T Ratio | | | |
| $R_{avg}$ (ng/dL) | 0.189 (0.070) | 0.233 (0.137) | 0.198 (0.041) |

[a] Values shown for half-life and time to maximum concentration are median and the range.
[b] Doses indicated are in T equivalents. Each TU capsule contained 158.3 mg TU, which corresponds to 100 mg T equivalents.

Mean serum T concentration during the 24-hour period post-dose ($C_{avg}$) indicated positive increases in serum T levels for all regimens studied, with the best response obtained in Regimen 3 ($C_{avg}$ 385 ng/dL). Mean peak serum T concentration observed in response to the oral T-ester preparations evaluated in this study never exceeded the upper limit of normal (i.e., 1100 ng/dL). And while some individual subjects did have $C_{max}$ T values above the normal upper limit, the vast majority of these peaks were in the range of 1200 to 1400 ng/dL. No subject in any treatment arm experienced a $C_{max}$ in excess of 1500 ng/dL.

Median serum T half-life ($T_{1/2}$) was approximately 15 hours for Regimens 1 and 2; for Regimen 3, $T_{1/2}$ was 8 hours. In each regimen, serum DHT concentrations increased in concert with serum T levels. The mean DHT:T ratios ($R_{avg}$) in all periods were modestly above the normal ranges as determined by liquid chromatography-mass spectroscopy (LC/MS/MS) (i.e., 0.03-0.1), but were clinically insignificant.

TU dosed at 200 mg T equivalents, BID with food yielded the most promising results with 75% of the subjects achieving a serum T $C_{avg}$ above 300 ng/dL (lower normal eugonadal limit). Similarly, 75% of the subjects achieved an average serum T within the normal range (i.e., 0.03-0.1 ng/dL). Those subjects that did not achieve a $C_{avg}$ of at least 300 ng/dL were all above 200 ng/dL, indicating that a modest increase in the TU dose would have been effective oral T replacement therapy in these subjects.

Serum T and DHT concentrations increased in concert in the majority of subjects regardless of T-ester dose with excellent dose linearity for oral TU was observed when data were corrected for serum T at baseline. Although DHT:T ratios were modestly elevated, any elevation was considered clinically insignificant. Less inter-subject variability was observed with the formulation than equivalent formulations of other T-esters (e.g., TE). Furthermore, in the "BID" dosing regimens, there was no difference in mean peak serum T concentrations or in the 12-hour AUCs between the morning and evening dose.

Concerning safety, although headache was reported as an adverse effect, in each treatment regimen, no adverse event was reported by more than one subject. No serious adverse events or deaths occurred during the study, and no subjects prematurely discontinued the study due to adverse events. Hence, all adverse events were considered to be of mild intensity.

Example 2—Seven-Day Study

Formulation B was studied for its acute tolerability and steady-state serum pharmacokinetic profile at two doses administered twice-daily to hypogonadal men. The study was designed as an open-label, repeat dose, cross-over, pharmacokinetic study (with food effect examined in one arm).

Twenty nine (29) hypogonadal men were enrolled after giving written informed consent, 24 of which completed the study. Each subject who completed the study received a regimen of Formulation B as follows:

1. 7 daily doses of 600 mg T as TU BID (300 mg/dose), i.e., 3 capsules/dose
2. 8 daily doses of 400 mg T as TU BID (200 mg/dose)

Doses were administered as capsules to subjects 30 minutes after initiation of meals (breakfast and dinner), except for Day 8, when the morning dose was administered fasting.

Peak exposure ($C_{max}$) to T and total exposure (AUC) to T were dose proportional after correction for the endogenous baseline T. The time of peak T concentrations ($T_{max}$) occurred at approximately 4 hours post-dose with each of the treatments. As well, the serum concentrations of both TU and DHTU rise and fall within the dosage interval with concentrations at the beginning and end of the dosing interval being less than 20% of the peak concentration for TU and less than 25% of the peak concentration for DHTU. Baseline T concentrations due to endogenous T production decreased progressively for each treatment. The observation is consistent with a progressive and persistent suppression of gonadotropins by exogenous T, thereby resulting in a decreased production of endogenous T. At least partial suppression was maintained over a 14-day washout period.

Again, serum T pharmacokinetics did not show diurnal variation with serum T concentrations. The night dose (administered at approximately 8 PM) produced a similar concentration-time profile as the morning dose (administered at approximately 8 AM) (FIG. 1). On account of the similarity between concentrations after AM and PM dosing (assessed in Regimen 1), 12-hour PK data from Regimen 2 (fed) were used to accurately predict a full 24-hour PK profile in response to 200 mg T (as TU), BID dosing. The simulated results indicated that (a) 77% of the subjects achieved a serum T $C_{avg}$ in the eugonadal range over the 24-hour period based on AUC thereby meeting the current FDA efficacy requirement of 75% for a T-replacement product; and (b) none of the subjects experienced a $C_{max}$ in excess of 1500 ng/dL, which is exceeds current FDA criteria that less than 85% of subjects have a $C_{max}$ of greater than 1500 ng/dL for a T-replacement product. Hence, also consistent with current FDA mandated efficacy endpoints, no subjects had a $C_{max}$ in excess of 2500 ng/dL and less than 5% of the subjects studied had a $C_{max}$ in the range of 1800-2500 ng/dL. It is noteworthy that these results were achieved in the absence of any dose adjustment.

Table 4 provides a comparison of steady state AM and PM pharmacokinetics of T with BID Dosing:

TABLE 4

| | Treatment Regimen 1 300 mg T, as TU, BID | |
|---|---|---|
| | AM Dose Mean ± SEM | PM Dose Mean ± SEM |
| $C_{max}$ (ng/dL) | 1410 ± 146 | 1441 ± 118 |
| $T_{max}$ (hr, time after dose) | 4.50 ± 0.39 | 5.9 ± 0.5 |
| $C_{min}$ (ng/dL) | 305 ± 30 | 324 ± 36 |
| $AUC_{0-12}$ (ng · hr/dL) | 9179 ± 754 | 9830 ± 659 |
| $C_{avg}$ (ng/dL) | 765 ± 63 | 819 ± 55 |
| FI ratio | 1.37 ± 0.09 | 1.36 ± 0.09 |
| $C_{min}/C_{max}$ ratio | 0.256 ± 0.029 | 0.243 ± 0.022 |

Administration of TU with a high-fat meal produced a similar serum T-concentration-time profile as administration with a standard meal. In contrast, administration of TU under fasting conditions resulted in greater than 50% decrease in serum T exposures ($C_{max}$ and AUC). Table 5. In all cases, a strong correlation between the observed $C_{max}$ and the calculated $C_{avg}$ was observed, suggesting that targeting of a particular $C_{avg}$ with the oral T-ester formulation can result in predictable peak T levels after dosing.

TABLE 5

|  | After High Fat Breakfast | | While Fasting | | |
| --- | --- | --- | --- | --- | --- |
|  | Arithmetic Mean | Geometric Mean | Arithmetic Mean | Geometric Mean | Geometric Mean of Individual Ratios |
| $C_{max}$ (ng/dL) | 955 | 854 | 394 | 365 | 0.426 |
| $AUC_{0-12}$ (ng · hr · dL) | 6217 | 5682 | 2894 | 2692 | 0.471 |

Administration under fed conditions (high fat breakfast) was used as the reference DHT concentrations tracked T concentrations, although DHT concentrations were only 11-34% of the T concentrations. Conversion of T to DHT showed a slight nonlinearity, increasing at a less than a concentration-proportional rate compared to T. The DHT/T ratio was least when T concentrations were highest, and the DHT/T ratio prior to starting TU treatment was approximately 0.1, while during treatment, at steady-state, the mean ratio was 0.24 and ranged from approximately 0.1 to 0.35 depending on the time of sampling after oral TU was administered.

Mean estradiol concentration prior to starting the oral TU treatment was approximately 11 pg/mL, and ranged from 19 pg/mL to 33 pg/mL on Day 7 of the various treatments (pre-dose concentrations). Pre-dose steady-state estradiol concentrations were approximately 20-30 pg/mL.

Example 3—Four-Week Study

Formulation B was also studied was to determine the time required to reach steady-state when hypogonadal men are treated for 28 days with twice daily dosing of 200 mg T (as TU) (i.e., 2 capsules/dose). The study was designed as an open-label, repeat dose, pharmacokinetic study.

Fifteen (15) hypogonadal men were enrolled after giving written informed consent, and all completed the study. Each subject received twice-daily doses of 200 mg T as TU for 28 days.

For each subject, the "Day 28" serial PK sampling day was scheduled for Day 32 of the study. Therefore, each dose-compliant subject received a total of 31 daily doses of 400 mg T as TU (i.e., 200 mg T, BID), and a final morning dose of 200 mg T as TU. Doses were administered as capsules, with subjects instructed to take doses 30 minutes after initiation of meals (breakfast and dinner).

Table 6 provides the relevant PK data from the study:

TABLE 6[a]

|  | T | DHT | DHT/T | $E_2$ |
| --- | --- | --- | --- | --- |
| $C_{max}$ or $R_{max}$[b] | 995 ± 436 (43.9%) ng/dL | 151 ± 75 (49.5%) ng/dL | 0.380 ± 0.181 (47.7%) ratio | 30.6 ± 14.9 (48.7%) pg/mL |
| $T_{max}$ | 4.87 ± 1.96 (40.3%) hr | 5.87 ± 2.80 (47.7%) hr | 5.87 ± 6.02 (102.7%) hr | 6.67 ± 3.09 (46.3%) hr |
| $C_{min}$ or $R_{min}$[b] | 199 ± 108 (54.2%) ng/dL | 64.6 ± 47.6 (73.8%) ng/dL | 0.131 ± 0.047 (36.0%) ratio | 15.4 ± 9.2 (59.9%) pg/mL |
| $C_{avg}$ or $R_{avg}$[b] | 516 ± 226 (43.7%) ng/dL | 109 ± 61 (55.8%) ng/dL | 0.245 ± 0.077 (31.5%) ratio | 22.0 ± 10.9 (49.8%) pg/mL |
| $AUC_{0-12}$ | 6197 ± 2708 (43.7%) ng · hr/dL | 1312 ± 732 (55.8%) ng · hr/dL | 2.94 ± 0.93 (31.5%) hr | 264 ± 131 (49.8%) pg · hr/mL |
| $C_{min}/C_{max}$ or $R_{min}/R_{max}$[b] | 23.5% ± 16.2% (69.0%) % | 41.5% ± 17.0% (40.9%) % | 37.3% ± 11.5% (30.8%) % | 50.2% ± 15.1% (30.0%) % |
| Absolute Change in $C_{baseline}$[c] | −168 ± 188 (112.2%) ng/dL | 3.50 ± 16.80 (480.1%) ng/dL | 0.197 ± 0.116 (59.0%) ratio | −0.405 ± 5.345 (1320.8%) pg/mL |
| Percent Change in $C_{baseline}$[c] | −53.4% ± 79.5% (148.8%) % | 18.8% ± 95.0% (506.6%) % | 267% ± 170% (63.8%) % | −1.9% ± 41.5% (2224.6%) % |
| Fluctuation Index | 156% ± 64% (40.8%) % | 84.7% ± 30.6% (36.1%) % | 96.0% ± 29.7% (30.9%) % | 74.5% ± 41.6% (55.9%) % |
| $\lambda_z$ | 0.0726 ± 0.0676 (93.1%) 1/hr | 0.0793 ± 0.0373 (47.1%) 1/hr | NA | 0.0544 ± 0.0176 (32.4%) 1/hr |
| $T_{1/2}$ | 29.0 ± 32.7 (112.8%) hr | 10.8 ± 5.8 (53.6%) hr | NA | 14.0 ± 5.3 (37.8%) hr |

[a]Results expressed as mean ± SEM. Co-efficient over variation is expressed as % in parentheses.
[b]$R_{max}$, $R_{min}$, $R_{avg}$ are the Maximum ratio, the Minimum ratio and the Time Averaged ratio, respectively for the DHT/T ratio (analogous to $C_{max}$, $C_{min}$ and $C_{avg}$)
[c]Change in Baseline determined as concentration (or ratio) in the final sample of Day 28 - concentration (or ratio) in the pre-treatment sample (Day 0).

86.7% of subjects achieved serum T $C_{avg}$ within the normal range, with no subjects having $C_{max}$ concentrations greater than 1800 ng/dL, and with just 13.3% of subjects having $C_{max}$ concentrations greater than 1500 ng/dL. (Note: No dosing adjustments were made during the conduct of this study to titrate subjects to be within the targeted efficacy and safety ranges.) The half-life of T in response to TU in the formulation tested was appreciably longer than has been reported for T alone or for TU given orally in prior art formulations. For example, in clinical studies of an oral TU formulation consistent with the invention described herein, an elimination half-life (a phase) of about approximately 5 hours was observed compared to a value estimated to be roughly half that (i.e., 2 to 3 hours) based on published serum T profiles after oral dosing of a prior art formulation of TU. A long elimination (i.e., terminal) half-life of 29 hrs was also observed with the inventive oral TU formulation. Endogenous T production was suppressed, however, by the administration of exogenous T, with only limited suppression occurring for the first 3 days, and requiring 5-7 days of continued treatment for maximal suppression.

Concentrations of T and DHT reached steady state by Day 7 of treatment. Concentrations of T and DHT were greater on Day 3 than on Day 5, indicating that a period of time was required for the exogenously administered T to suppress endogenous T production thus enabling achievement of steady-state in response to oral TU. Indeed, addition of the exogenous T suppressed endogenous T levels from 276 ng/dL pretreatment to 108 ng/dL after 28 days of supplementary T treatment.

Figure 2:
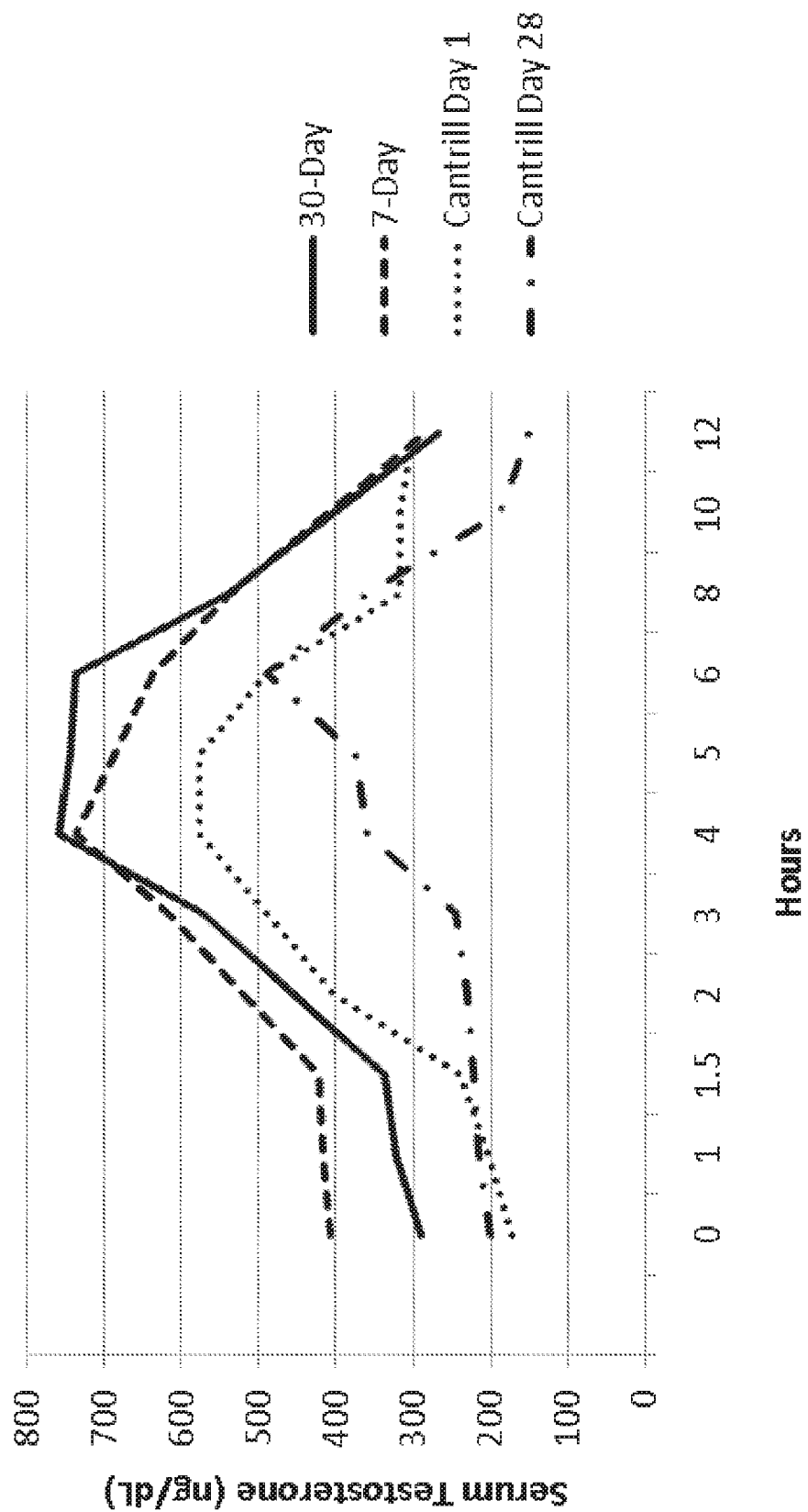
FIG. 2 shows a serum T response over time in hypogonadal men upon administration of a formulation of the invention vs. a conventional oral TU formulation comprising TU in oleic acid (Restandol).

Significantly, however, once steady state was achieved for serum T in response to twice-daily oral TU, little to no decline in serum T response was observed over time (i.e., no trend toward lower serum T level with continued TU dosing). For example, the $C_{avg}$ at Day 15 was substantially similar to the $C_{avg}$ observed at day 28 (FIG. 2). By contrast, oral TU formulations in the art have been reported to trend toward a lower mean T over time (Cantrill, J. A. *Clinical Endocrinol* (1984) 21: 97-107). In hypogonadal men treated with a formulation of oral TU, known in the art, it has been reported that the serum T response observed after 4 weeks of therapy was about 30% less than that observed on the initial day of therapy in hypogonadal men—most of whom had a form of primary hypogonadism and thus low baseline levels of serum T (e.g., <100 ng/dL), so the decrease in T cannot be explained by suppression of endogenous T alone].

Serum DHT concentrations closely tracked T concentrations, with DHT and DHT/T values increasing 4 to 7 fold during treatment. Average DHT/T ratio over a 12-hour dosing interval was 0.245, although values over the dosing interval ranged from a mean maximum ratio of 0.380 to a mean minimum ratio of 0.131. DHT concentrations returned to pretreatment levels within 36 hours of discontinuing treatment with oral TU. However, T concentrations did not return to pretreatment levels as quickly, ostensibly because of the suppression of endogenous T production/release is not as rapidly reversed.

Concentrations of estradiol (E2) showed a monotonic, progressive increase to the steady state, which was also reached by Day 7 of treatment. E2 concentrations also showed systematic variation over the dosing interval that tracked the changes in T. The mean $C_{max}$, $C_{avg}$, and $C_{min}$ values for E2 were 30.6 pg/mL, 22.0 pg/mL and 15.5 pg/mL, respectively. E2 concentrations returned to pretreatment levels within 36 hours of discontinuing treatment with oral TU.

Mean $C_{max}$, $C_{avg}$, and $C_{min}$ concentrations at steady state (morning dose of Day 28) for T were 995 ng/dL, 516 ng/dL and 199 ng/dL, respectively. Median Tmax for T occurred at 5.0 hours post dose. $C_{min}$ averaged 23.5% of $C_{max}$, resulting in a Fluctuation Index of 156%. The elimination half-life of T could only be evaluated in about half the subjects, and its median value in those subjects was 18.4 hours (mean $T_{1/2}$ was 29 hours).

Example 4—Food Effects Study

Any effect of dietary fat on the pharmacokinetics of Formulation B in hypogonadal men was studied in an open-label, two-center, five-way crossover study. After a washout period of 4-10 days, a single dose of 300 mg of T (475 mg TU, 3 capsules of Formulation B) was administered to sixteen hypogonadal men with serum a baseline T level 205.5±25.3 ng/dL (mean±SE, range 23-334.1 ng/dL). Subjects were randomized to receive the drug in the fasting state or 30 minutes after consumption of meals containing ~800 calories with specific amounts of fat (wt %): very low fat (6-10%); low fat (20%); "normal" diet fat (30%); or high fat (50%). The "normal" diet was, a priori, established as the comparator (i.e., reference diet) for purposes of statistical comparisons. Serial blood samples were collected for a total of 24 hours after drug administration to determine serum testosterone and dihydrotestosterone (DHT) levels by liquid chromatography-mass spectroscopy (LC/MS/MS).

Figure 3:
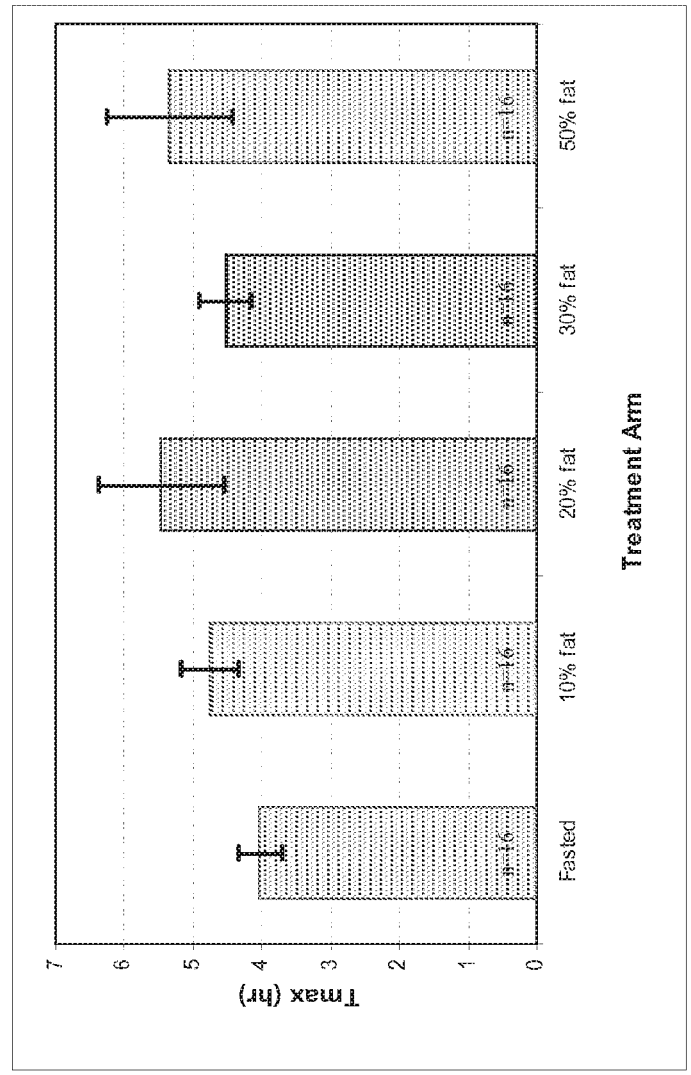
FIG. 3 provides $T_{max}$ values of serum T levels in subjects having consumed meals of varying fat content (as a percentage by weight) prior to oral administration of a TU formulation of the invention.
Figure 4:
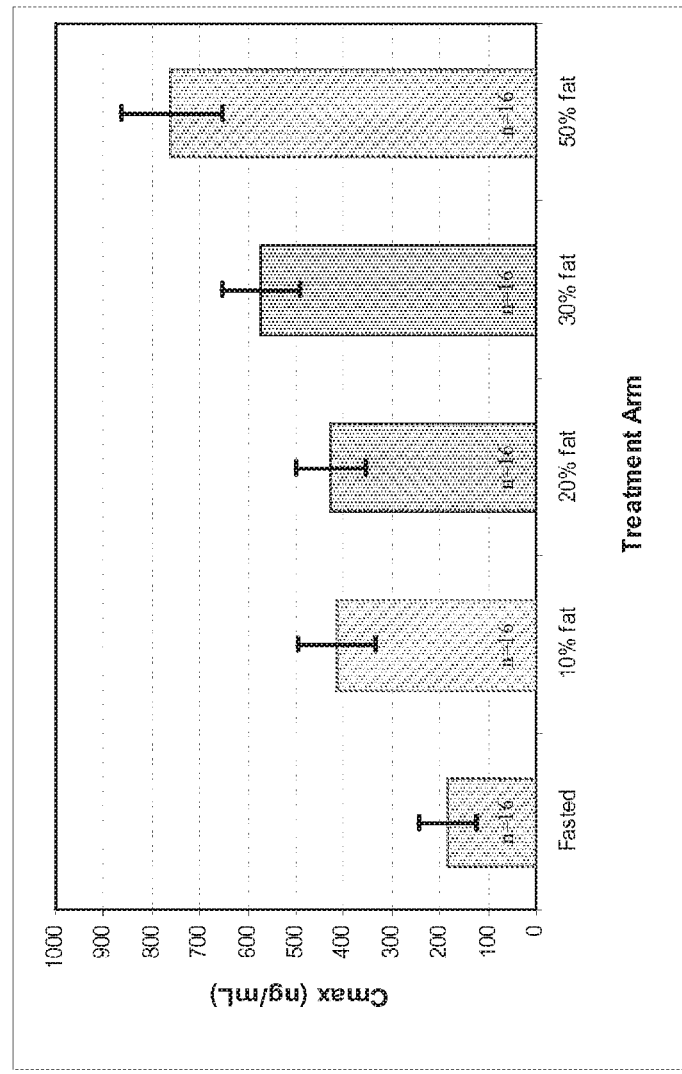
FIG. 4 provides $C_{max}$ values of serum T levels in subjects having consumed meals of varying fat content (as a percentage by weight) prior to oral administration of a TU formulation of the invention.
Figure 5:
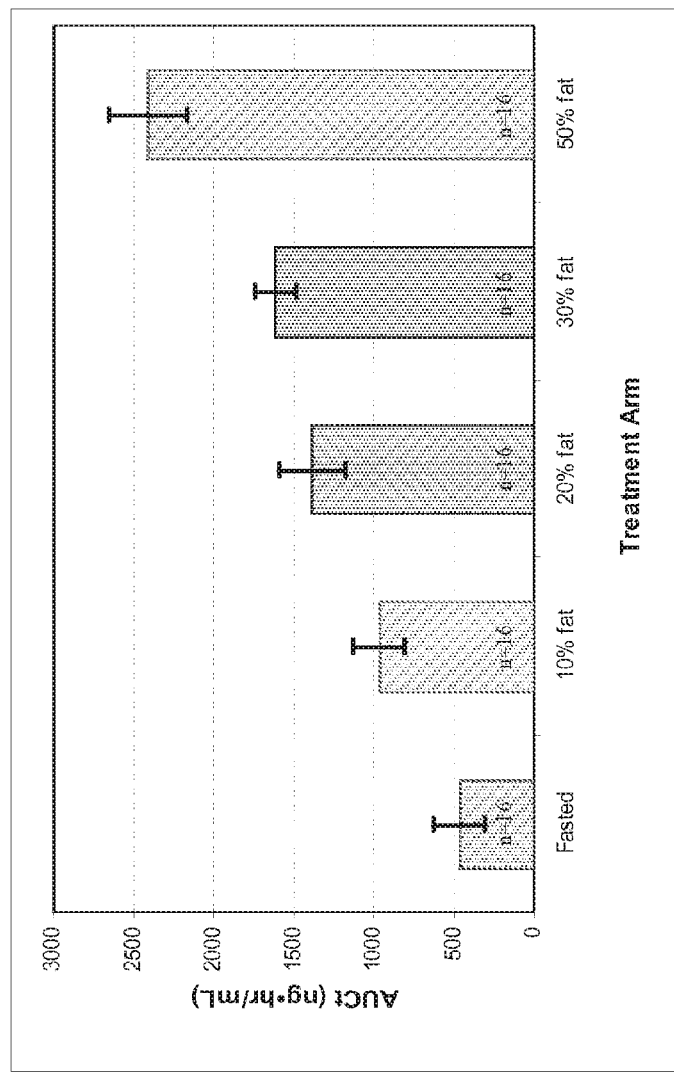
FIG. 5 provides area under the curve (AUC) values of serum T levels in subjects having consumed meals of varying fat content (as a percentage by weight) prior to oral administration of a TU formulation of the invention.

Pharmacokinteic parameters (Table 7, FIGS. 3-5) observed for serum T in response to a single, high-dose of oral TU were found to be similar for a low-fat and normal fat diet—in fact so much so that they were bioequivalent (i.e., the 90% confidence interval was between 85-125%). Similar serum T PK parameters were also observed when the normal- and high-fat meals were compared. And although the high-fat meal yielded a greater serum T response (albeit not statistically different), the mean ratio of least square means fell within 70-143% when compared to the normal-fat meal—a clinically insignificant difference of <30%.

TABLE 7

| | Serum T pharmacokinetic parameters (mean ± SD) in response to oral TU administered with different diets | | | | |
|---|---|---|---|---|---|
| | Fasting | 6-10% Fat | 20% Fat | 30% Fat | 50% Fat |
| $C_{Avg}{}^1$ (ng/dL) | 526 ± 324 | 781 ± 385 | 884 ± 505 | 1010 ± 356 | 1260 ± 477 |
| $C_{Max}$ (ng/dL) | 948 ± 798 | 1370 ± 732 | 1520 ± 711 | 1760 ± 598 | 2140 ± 901 |
| $T_{Max}$ (hr) | 4.1 ± 0.96 | 4.9 ± 1.8 | 6.3 ± 3.9 | 5.1 ± 1.5 | 6.4 ± 4.9 |
| AUC (ng * h/dL) | 7796 ± 3673 | 10855 ± 4285 | 12477 ± 5028 | 13639 ± 3773 | 16464 ± 5584 |

[1]$C_{Avg}$ is calculated as $AUC_{0-\infty}/\tau$ ($\tau$ = dosing interval = 12 hours for BID dosing)

Variability in PK response appeared to be highest following the first dose, or first few doses of oral TU, and decreased as therapy continued. Consequently, any impact of dietary fat across the range of low-normal-high on serum T PK parameters is likely to be insignificant during chronic dosing. This stance is consistent with the PK findings from the 7-day treatment (Example 2) and from the 30-day treatment (Example 3), where repeat dose studies of oral TU where the PK under the differing meal conditions still showed similar results for Cmax and Cavg distributions [both studies administered 200 mg T (as TU), BID].

Statistical comparisons of the serum T response observed after oral TU was taken without food or with a very low fat, low fat, or high fat diet versus a normal fat diet (i.e., reference diet) revealed that there was no statistically significant difference at the $p<0.05$ level between the low-fat or high-fat diets versus the normal diet. Conversely, administration of oral TU as a SEDDS formulation while fasting or with a very low-fat breakfast yielded serum T PK parameters significantly different (i.e., lower) from a normal diet. Accordingly, the fat content of meals taken with the inventive formulations can differ substantially from "normal", without a clinically significant impact on the levels of T obtained. Thus, a patient is permitted flexibility in eating habits from meal to meal, and from day to day, which could not have been heretofore possible with known oral TU formulations. Oral TU formulations known in the art have heretofore been unable to achieve any meaningful serum T levels in the fasted state.

Example 5—In Vitro Dissolution Tests

Dissolution studies of formulations of the present invention were studied in vitro to assess their correlation with the PK profiles observed in vivo. In a first study, the dissolution of Formulation B was studied. Andriol Testocaps® (40 mg TU per softgel dissolved in a mixture of castor oil and propylene glycol laurate) was included for comparison. The study was conducted with essentially equivalent doses of TU, i.e., 1 capsule of Formulation B (158.3 mg TU) and 4 softgels of Testocaps (4×40 mg=160 mg TU). The dissolution (i.e., the release of TU from the respective formulations) was studied in Fed State Simulated Intestinal Fluid (FeSSIF) medium, which simulates intestinal fluid upon stimulation by a meal. FeSSIF contains sodium hydroxide, glacial acetic acid, potassium chloride, lecithin, and sodium taurocholate. The final emulsion is adjusted to pH 5.0.

That data are presented in Tables 8 and 9 demonstrate that the inventive formulation released approximately 40% TU within the first 30 minutes and about 60% of the total capsule after 4 hours. For the Testocaps®, however, there is little to no drug released (1%) for the entire 4 hours. The observed major difference in the dissolution of TU from these two formulations can be attributed, at least in part, to the presence of the hydrophlic surfactant, e.g., Cremophor RH40, in Formulation B. In contrast, Andriol Testocaps® (incorporate an oil (Castor Oil) and a lipophilic surfactant (Propylene Glycol Laureate) only.

TABLE 8

% Release of TU from Formulation B

| Time | % Released | | | |
|---|---|---|---|---|
| (Hours) | 1 | 2 | 3 | Average |
| 0.5 | 39.3 | 39.2 | 34.6 | 37.7 |
| 1 | 46.2 | 43.6 | 44.3 | 44.7 |
| 2 | 52.8 | 50.9 | 49.8 | 51.2 |

TABLE 8-continued

% Release of TU from Formulation B

| Time | % Released | | | |
|---|---|---|---|---|
| (Hours) | 1 | 2 | 3 | Average |
| 4 | 62.7 | 61.7 | 61.3 | 61.9 |
| Infinity | 96.0 | 100.1 | 90.9 | 95.6 |

TABLE 9

% Release of TU from Andriol Testocaps ®

| Time | % Released | | | |
|---|---|---|---|---|
| (Hours) | 1 | 2 | 3 | Average |
| 0.5 | 0.0 | 0.0 | 0.0 | 0.0 |
| 1 | 0.0 | 0.0 | 0.0 | 0.0 |
| 2 | 0.0 | 0.9 | 0.0 | 0.3 |
| 4 | 1.3 | 1.1 | 1.3 | 1.3 |
| Infinity | 3.9 | 3.6 | 1.5 | 3.0 |

In a second study, Formulation A was subjected to a similar assay, but using a 5% Triton X100 potassium phosphate buffer (pH 6.8) as a dissolution medium. The results are provided in Table 10 below. In this study, 98% of the TU from the inventive formulation was released within the first 15 minutes of dissolution and once again the presence of the hydrophilic surfactant Cremophor RH40 has certainly facilitated this fast dissolution and TU release.

TABLE 10

% Release of TU from Formulation A

| Time | % Released | | | | | | |
|---|---|---|---|---|---|---|---|
| (M) | 1 | 2 | 3 | 4 | 5 | 6 | Average |
| 0 | 0.0 | 0.0 | 0.0 | 0.0 | 0.0 | 0.0 | 0.0 |
| .25 | 98.9 | 96.9 | 97.7 | 95.7 | 96.6 | 101.0 | 97.8 |
| 0.5 | 98.9 | 97.8 | 98.4 | 98.3 | 97.5 | 100.0 | 98.5 |
| 1.0 | 99.5 | 98.2 | 98.0 | 98.4 | 98.1 | 100.2 | 98.7 |

In yet another embodiment of the present invention, the pharmaceutical compositions disclosed herein may also be suitable for ameliorating some of the side-effects of certain strategies for male contraception. For example, progestin-based male contraception substantially suppresses luteinizing hormone (LH) and follicle-stimulating hormone (FSH), and thereby suppresses spermatogenesis, resulting in clinical azoospermia (defined as less than about 1 million sperm/mL semen for 2 consecutive months). However, administration of progestins also has the undesirable side-effect of significantly reducing steady-state serum testosterone levels.

In such situations, for example, it may be preferable to provide preparations of progestin concomitantly with testosterone or a testosterone derivative (e.g., TU). More preferably, a pharmaceutical preparation according to the invention is provided, comprising progestin—in an amount sufficient to substantially suppress LH and FSH production—in combination with testosterone. In some embodiments, the pharmaceutical preparation is for once-daily, oral delivery.

Formulations of the present invention can provide extended release formulations that can deliver testosterone into the serum over several hours. Indeed, the half-life of serum testosterone according to the invention is between 3 and 7 hours, preferably greater than 4, 5, or 6 hours. The serum half-life of testosterone in men, by contrast, is considered to be in the range of 10 to 100 minutes.

Without being bound by or limited to theory, it is believed that the inventive formulations achieve these results, in one aspect, by enhancing absorption of a medicament therein by the intestinal lymphatic system rather than by way of portal circulation. In another aspect, again without being bound by or limited to theory, it is believed that by using an ester of testosterone, the time required for de-esterification to occur contributes to a longer T half-life.

Oral dosages of the present invention can be taken by a patient in need of testosterone therapy once every about twelve hours to maintain desirable levels of serum testosterone. In a more preferred embodiment, oral dosages are taken by a patient in need of testosterone therapy once every about twenty four hours. In general, "desirable" testosterone levels are those levels found in a human subject characterized as not having testosterone deficiency.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method of treating testosterone deficiency or its symptoms in a male in need thereof comprising:
   daily administering to said male about 475 mg testosterone undecanoate,
   wherein said testosterone undecanoate is administered in an oral pharmaceutical composition with food, and
   wherein said oral pharmaceutical composition comprises:
      18-22 percent by weight of solubilized testosterone undecanoate;
      50-55 percent by weight of oleic acid;
      15-17 percent by weight of polyoxyethylene (40) hydrogenated castor oil; and
      10-15 percent by weight of a mixture of borage seed oil and peppermint oil.

2. The method of claim 1, wherein said oral pharmaceutical composition comprises about 20 percent by weight testosterone undecanoate.

3. The method of claim 1, wherein said oral pharmaceutical composition comprises:
   19.8 percent by weight of solubilized testosterone undecanoate;
   51.6 percent by weight of oleic acid;
   16.1 percent by weight of polyoxyethylene (40) hydrogenated castor oil;
   10 percent by weight of borage seed oil; and
   2.5 percent by weight of peppermint oil.

4. The method of claim 3, wherein said oral pharmaceutical composition further comprises one or more antioxidants.

5. The method of claim 1, wherein said oral pharmaceutical composition is in the form of a capsule.

6. The method of claim 1, wherein said administration results in a serum testosterone $C_{ave}$ in said male in the range of from about 300-1100 ng/dL.

7. The method of claim 1, wherein said oral pharmaceutical composition is administered once daily.

8. The method of claim 1, wherein said oral pharmaceutical composition is administered twice daily.

9. The method of claim 8, wherein said administration results in a serum testosterone $C_{ave}$ in said male in the range of from about 300-1100 ng/dL.

10. The method of claim 1, wherein said male has primary hypogonadism.

11. A method of treating testosterone deficiency or its symptoms in a male having primary hypogonadism comprising:
   daily administering to said male about 475 mg testosterone undecanoate,
   wherein said testosterone undecanoate is administered in an oral pharmaceutical composition, and
   wherein said oral pharmaceutical composition is administered twice daily with food and comprises:
      19.8 percent by weight of solubilized testosterone undecanoate;
      51.6 percent by weight of oleic acid;
      16.1 percent by weight of polyoxyethylene (40) hydrogenated castor oil;
      10 percent by weight of borage seed oil; and
      2.5 percent by weight of peppermint oil.

12. The method of claim 11, wherein said administration results in a serum testosterone $C_{ave}$ in said male in the range of from about 300-1100 ng/dL.

* * * * *